(12) United States Patent
Pitard

(10) Patent No.: US 11,179,478 B2
(45) Date of Patent: Nov. 23, 2021

(54) CAPPED AND UNCAPPED RNA MOLECULES AND BLOCK COPOLYMERS FOR INTRACELLULAR DELIVERY OF RNA

(71) Applicants: Institut National de la Sante et de la Recherche Medicale (INSERM), Paris (FR); Universite de Nantes, Nantes (FR); Centre National de la Recherche Scientifique, Paris (FR)

(72) Inventor: Bruno Pitard, Nantes (FR)

(73) Assignees: INSTITUT NATIONAL DE LA SANTE ET DE LA RECHERCHE MEDICALE (INSERM), Paris (FR); UNIVERSITE DE NANTES, Nantes (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/129,912

(22) PCT Filed: Apr. 1, 2015

(86) PCT No.: PCT/IB2015/052405
§ 371 (c)(1),
(2) Date: Sep. 28, 2016

(87) PCT Pub. No.: WO2015/151048
PCT Pub. Date: Oct. 8, 2015

(65) Prior Publication Data
US 2017/0209597 A1 Jul. 27, 2017

(30) Foreign Application Priority Data
Apr. 1, 2014 (EP) .................................. 14305472.4

(51) Int. Cl.
*A61K 48/00* (2006.01)
*C08G 65/333* (2006.01)
*A61K 47/34* (2017.01)
*C12N 15/88* (2006.01)
*C08G 65/32* (2006.01)
*A61K 38/18* (2006.01)
*A61K 38/47* (2006.01)

(52) U.S. Cl.
CPC ...... *A61K 48/0041* (2013.01); *A61K 38/1816* (2013.01); *A61K 38/47* (2013.01); *A61K 47/34* (2013.01); *A61K 48/0033* (2013.01); *C08G 65/32* (2013.01); *C08G 65/33306* (2013.01); *C12N 15/88* (2013.01); *C12Y 302/01023* (2013.01); *C08G 2650/04* (2013.01); *C08G 2650/38* (2013.01); *C08G 2650/50* (2013.01)

(58) Field of Classification Search
None
See application file for complete search history.

(56) References Cited

U.S. PATENT DOCUMENTS

| | | | | |
|---|---|---|---|---|
| 6,706,694 B1 * | 3/2004 | Wolff | ...................... | A61K 48/00 424/130.1 |
| 2003/0206910 A1 * | 11/2003 | Nicol | ...................... | A61K 39/00 424/178.1 |
| 2013/0156849 A1 * | 6/2013 | de Fougerolles | ...... | A61K 48/00 424/450 |

FOREIGN PATENT DOCUMENTS

| | | | | |
|---|---|---|---|---|
| WO | WO 03/018603 | 3/2003 | | |
| WO | WO 03/066104 | 8/2003 | | |
| WO | WO-2007024708 A2 * | 3/2007 | ......... | A61K 48/0041 |
| WO | WO 2010/026537 | 3/2010 | | |
| WO | WO 2013/128423 | 9/2013 | | |

OTHER PUBLICATIONS

Beilvert et al., DNA/Amphiphilic Block Copolymer Nanospheres Reduce Asthmatic Response in a Mouse Model of Allergic Asthma. Human Gene Therapy 23:597-608 (Jun. 2012). (Year: 2012).*
Adel-Patient et al., Block Copolymers Have Differing Adjuvant Effects on the Primary Immune Response Elicited by Genetic Immunization and on Further Induced Allergy. Clinical and Vaccine Immunology, Jan. 2010, p. 36-42 vol. 17, No. 1 (Year: 2010).*
Kariko et al., Increased Erythropoiesis in Mice Injected With Submicrogram Quantities of Pseudouridinecontaining mRNA Encoding Erythropoietin. Mol Ther, 2012,20:948-953. (Year: 2012).*
Cheng et al., *Multifunctional triblock copolymers for intracellular messenger RNA delivery*, 33 Biomaterials 6868-6876 (2012).
Debus et al., *Delivery of messenger RNA using poly(ethylene imine)-poly(ethylene glycol)-copolymer blends for polyplex formation: Biophysical characterization and in vitro transfection properties*, 148 Journal of Controlled Release 334-343 (2010).
McIlroy et al., *DNA/Amphiphilic Block Copolymer Nanospheres Promote Low-dose DNA Vaccination*, 17(8) Molecular Therapy 1473-1481 (Aug. 2009).
Uchida et al., In Vivo *Messenger RNA Introduction into the Central Nervous System Using Polyplex Nanomicelle*, 8(2) PLOS One pp. 1-8 (Feb. 2013).
International Search Report dated Aug. 18, 2016, in corresponding PCT Application No. PCT/IB2015/052405.
Tavernier et al., *mRNA as gene therapeutic: How to control protein expression*, 150 Journal of Controlled Release 238-247 (2011).

* cited by examiner

*Primary Examiner* — Arthur S Leonard
(74) *Attorney, Agent, or Firm* — Buchanan Ingersoll & Rooney PC

(57) ABSTRACT

The present invention relates to the use of at least one tetra functional non-ionic amphiphilic block copolymer as a vehicle for capped or uncapped mRNA for intracellular delivery for gene therapy.

Figure 1A:
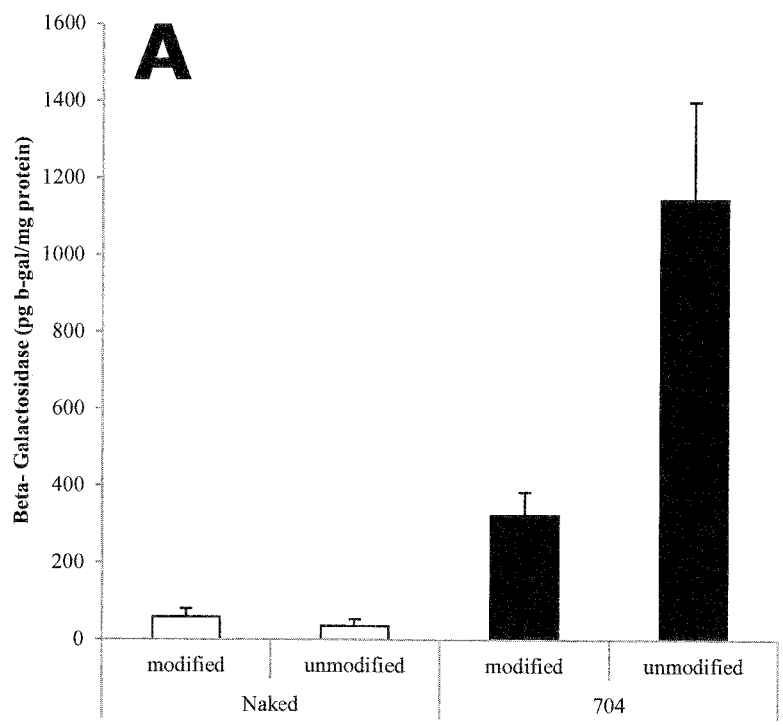

11 Claims, 16 Drawing Sheets
Specification includes a Sequence Listing.

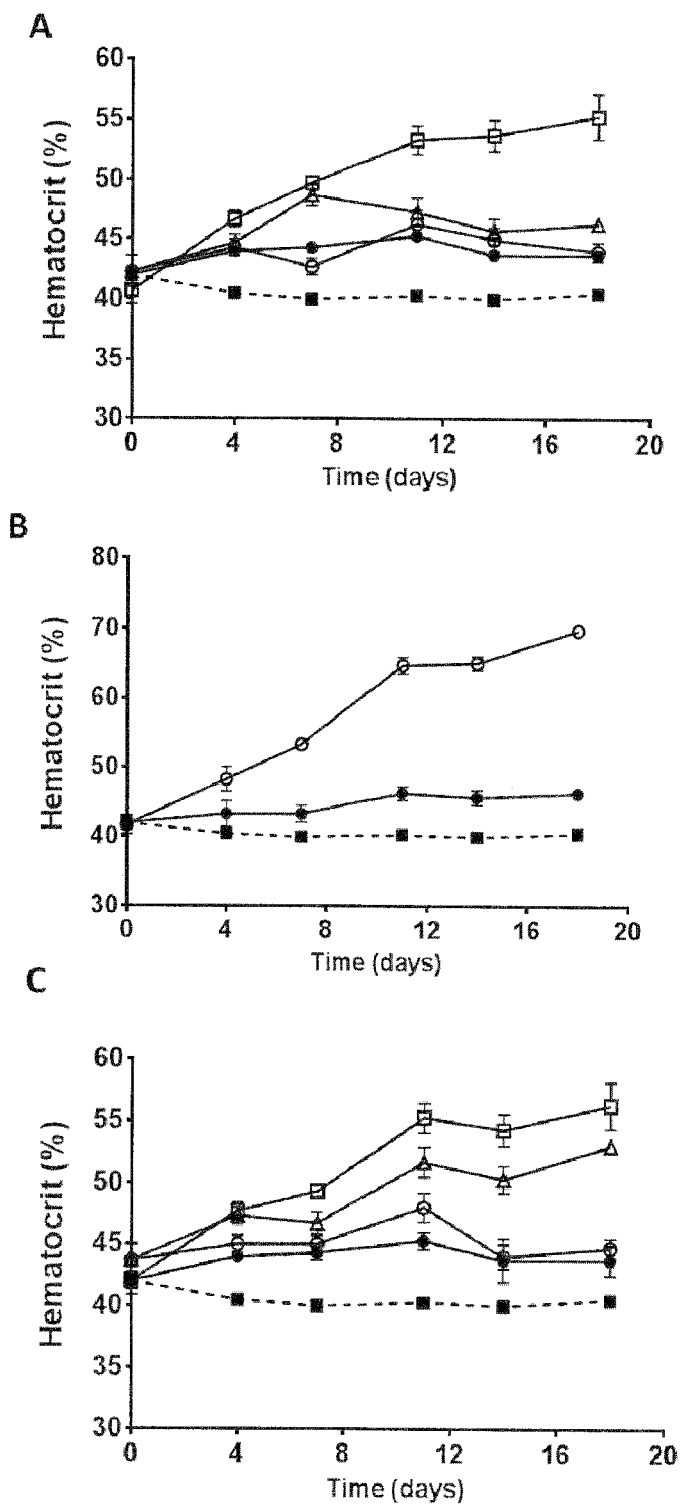
Figures 3, A, B, C

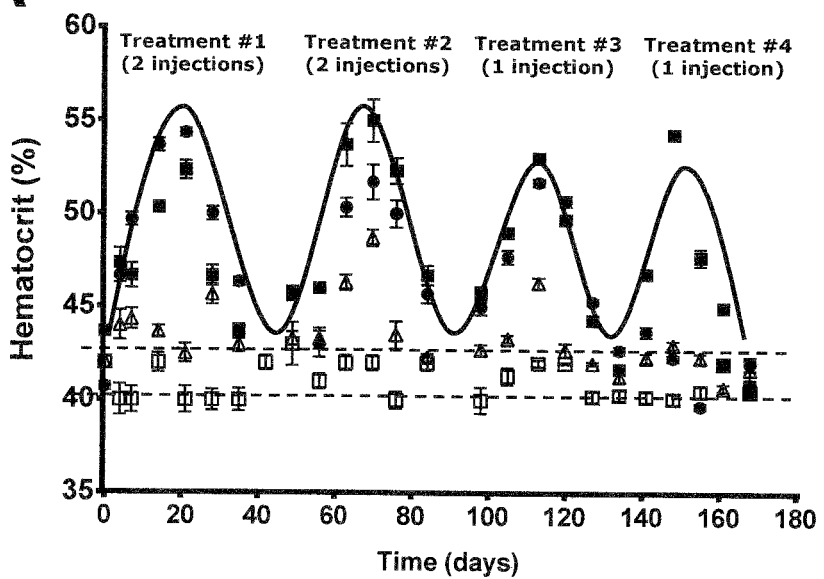
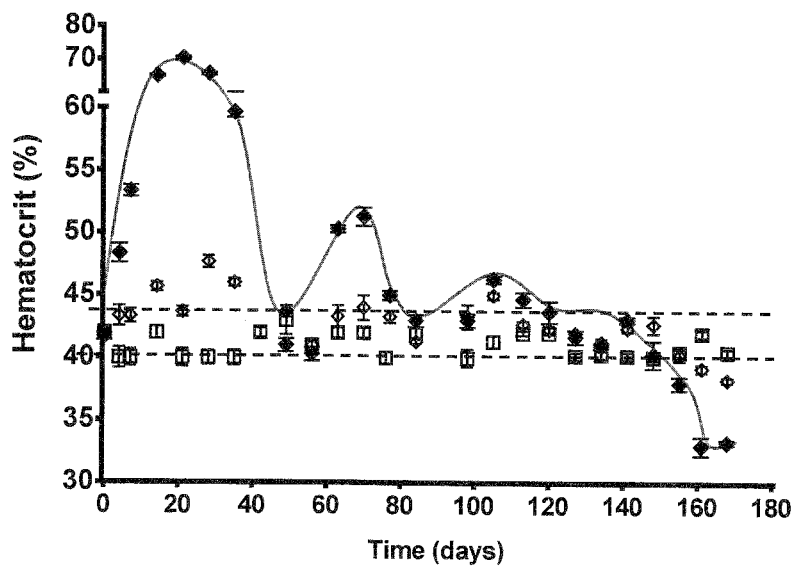
Figures 4, A, B,

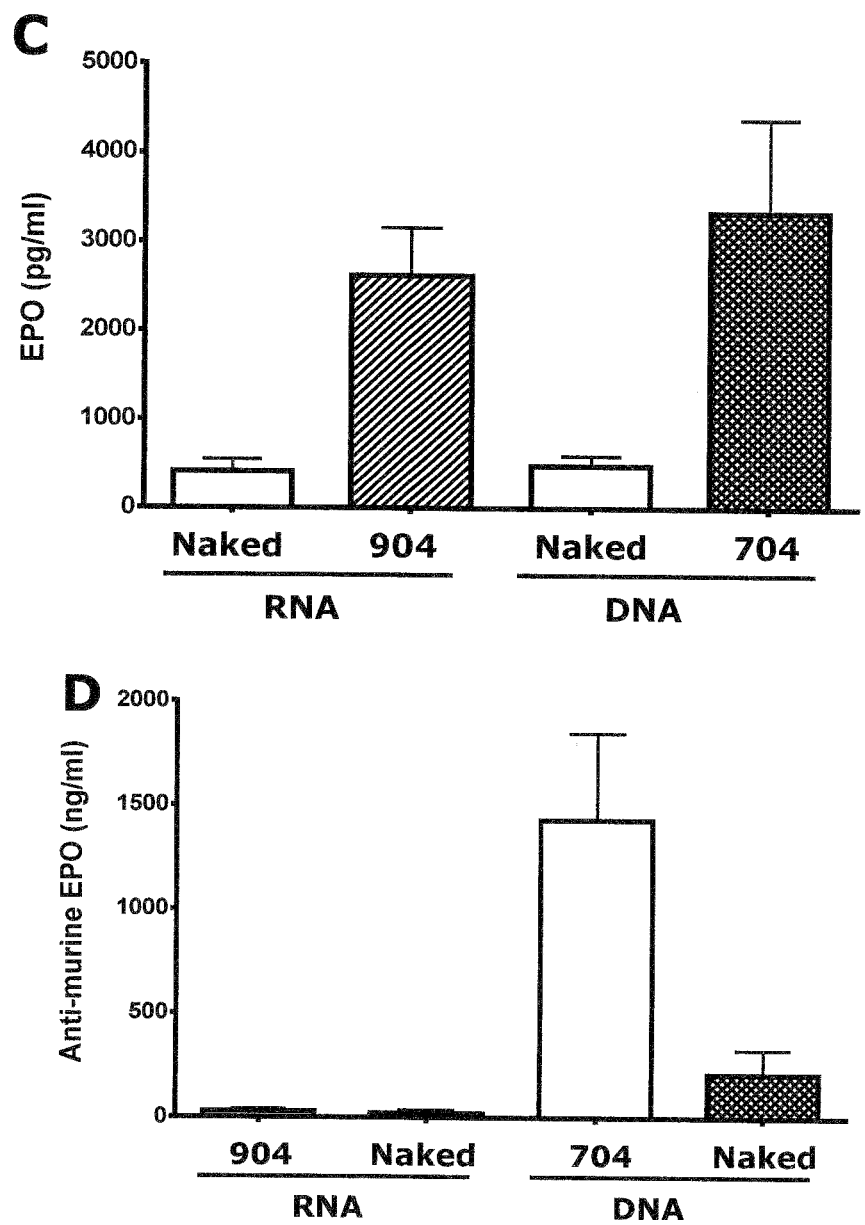
Figures 4, C, D

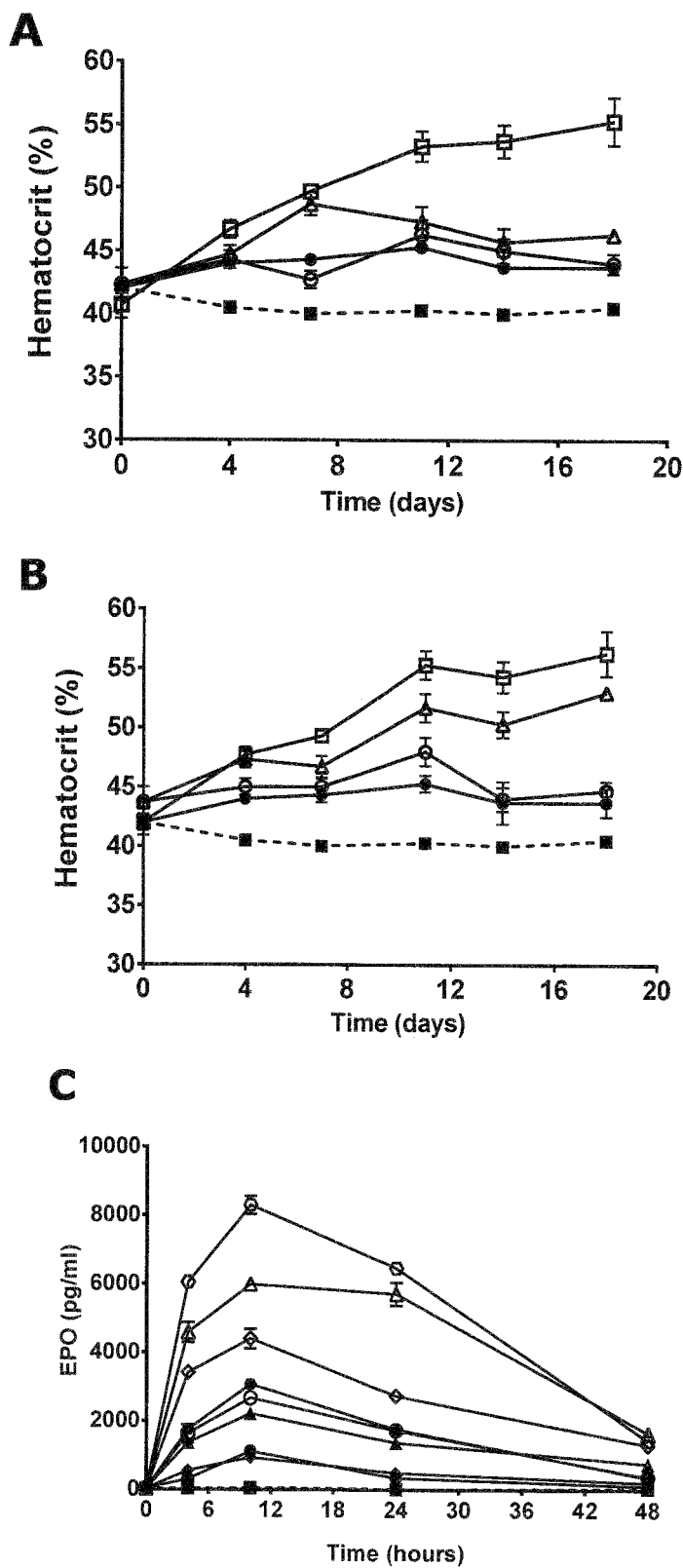
Figure 11 A, B, C

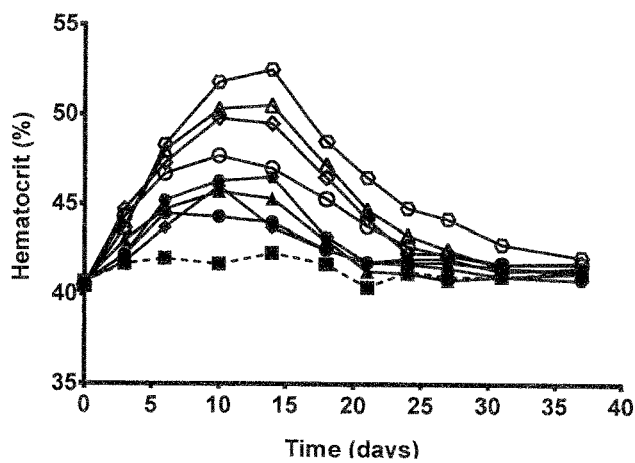
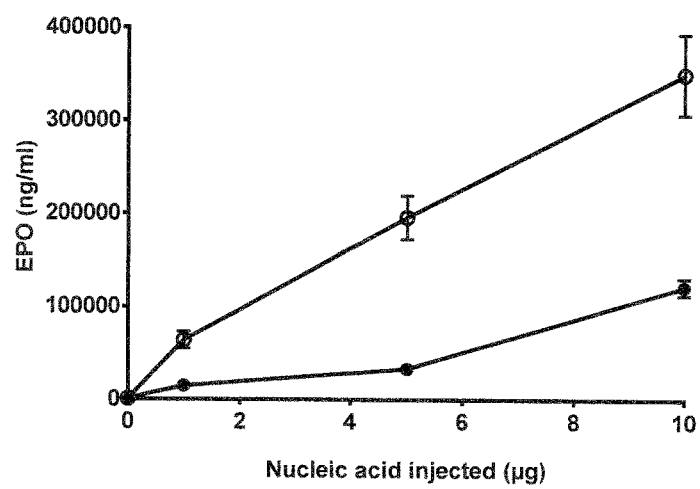
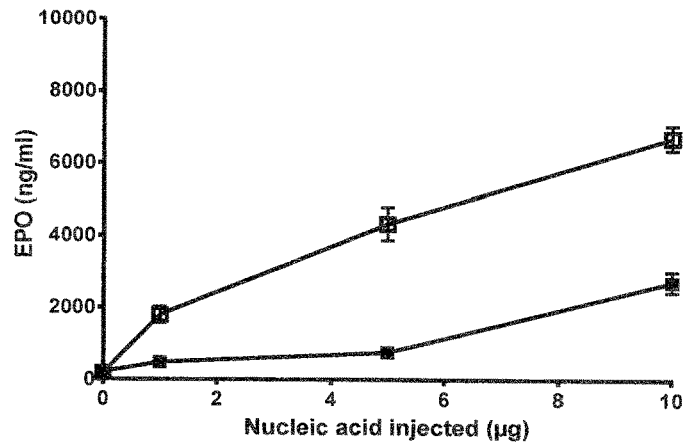
Figure 11 D, E, F

SEQUENCE LISTING

<160> NUMBER OF SEQ ID NOS: 5

<210> SEQ ID NO 1
<211> LENGTH: 3144
<212> TYPE: DNA
<213> ORGANISM: Escherichia coli

<400> SEQUENCE: 1

| | | | | | | |
|---|---|---|---|---|---|---|
| atgtcgttta | ctttgaccaa | caagaacgtg | attttcgttg | ccggtctggg | aggcattggt | 60 |
| ctggacacca | gcaaggagct | gctcaagcgc | gatcccgtcg | ttttacaacg | tcgtgactgg | 120 |
| gaaaaccctg | gcgttaccca | acttaatcgc | cttgcagcac | atccccttt | cgccagctgg | 180 |
| cgtaatagcg | aagaggcccg | caccgatcgc | ccttcccaac | agttgcgcag | cctgaatggc | 240 |
| gaatggcgct | ttgcctggtt | tccggcacca | gaagcggtgc | cggaaagctg | gctggagtgc | 300 |
| gatcttcctg | aggccgatac | tgtcgtcgtc | ccctcaaact | ggcagatgca | cggttacgat | 360 |
| gcgcccatct | acaccaacgt | aacctatccc | attacggtca | atccgccgtt | tgttcccacg | 420 |
| gagaatccga | cgggttgtta | ctcgctcaca | tttaatgttg | atgaaagctg | gctacaggaa | 480 |
| ggccagacgc | gaattatttt | tgatggcgtt | aactcggcgt | tcatctgtg | gtgcaacggg | 540 |
| cgctgggtcg | gttacggcca | ggacagtcgt | ttgccgtctg | aatttgacct | gagcgcattt | 600 |
| ttacgcgccg | gagaaaaccg | cctcgcggtg | atggtgctgc | gttggagtga | cggcagttat | 660 |
| ctggaagatc | aggatatgtg | gcggatgagc | ggcattttcc | gtgacgtctc | gttgctgcat | 720 |
| aaaccgacta | cacaaatcag | cgatttccat | gttgccactc | gctttaatga | tgatttcagc | 780 |
| cgcgctgtac | tggaggctga | agttcagatg | tgcggcgagt | tgcgtgacta | cctacgggta | 840 |
| acagtttctt | tatggcaggg | tgaaacgcag | gtcgccagcg | gcaccgcgcc | tttcggcggt | 900 |

```
gaaattatcg atgagcgtgg tggttatgcc gatcgcgtca cactacgtct gaacgtcgaa    960
aacccgaaac tgtggagcgc cgaaatcccg aatctctatc gtgcggtggt tgaactgcac   1020
accgccgacg gcacgctgat tgaagcagaa gcctgcgatg tcggtttccg cgaggtgcgg   1080
attgaaaatg gtctgctgct gctgaacggc aagccgttgc tgattcgagg cgttaaccgt   1140
cacgagcatc atcctctgca tggtcaggtc atggatgagc agacgatggt gcaggatatc   1200
ctgctgatga agcagaacaa ctttaacgcc gtgcgctgtt cgcattatcc gaaccatccg   1260
ctgtggtaca cgctgtgcga ccgctacggc ctgtatgtgg tggatgaagc caatattgaa   1320
acccacggca tggtgccaat gaatcgtctg accgatgatc cgcgctggct accggcgatg   1380
agcgaacgcg taacgcgaat ggtgcagcgc gatcgtaatc acccgagtgt gatcatctgg   1440
tcgctgggga tgaatcagg ccacggcgct aatcacgacg cgctgtatcg ctggatcaaa   1500
tctgtcgatc cttcccgccc ggtgcagtat gaaggcggcg gagccgacac cacggccacc   1560
gatattattt gcccgatgta cgcgcgcgtg gatgaagacc agcccttccc ggctgtgccg   1620
aaatggtcca tcaaaaaatg gctttcgcta cctggagaga cgcgcccgct gatcctttgc   1680
gaatacgccc acgcgatggg taacagtctt ggcggtttcg ctaaatactg gcaggcgttt   1740
cgtcagtatc cccgtttaca gggcggcttc gtctgggact gggtggatca gtcgctgatt   1800
aaatatgatg aaaacggcaa cccgtggtcg gcttacggcg gtgattttgg cgatacgccg   1860
aacgatcgcc agttctgtat gaacggtctg gtctttgccg accgcacgcc gcatccagcg   1920
ctgacggaag caaaacacca gcagcagttt ttccagttcc gtttatccgg caaaccatc   1980 gaagtgacca gcgaatacct gttccgtcat agcgataacg agctcctgca ctggatggtg   2040
gcgctggatg gtaagccgct ggcaagcggt gaagtgcctc tggatgtcgc tccacaaggt   2100
aaacagttga ttgaactgcc tgaactaccg cagccggaga gcgccgggca actctggctc   2160
acagtacgcg tagtgcaacc gaacgcgacc gcatggtcag aagccgggca catcagcgcc   2220
tggcagcagt ggcgtctggc ggaaaacctc agtgtgacgc tccccgccgc gtcccacgcc   2280
atcccgcatc tgaccaccag cgaaatggat ttttgcatcg agctgggtaa taagcgttgg   2340
caatttaacc gccagtcagg cttctctttca cagatgtgga ttggcgataa aaaacaactg   2400
ctgacgccgc tgcgcgatca gttcacccgt gcaccgctgg ataacgacat tggcgtaagt   2460
gaagcgaccc gcattgaccc taacgcctgg gtcgaacgct ggaaggcggc gggccattac   2520
caggccgaag cagcgttgtt gcagtgcacg gcagatacac ttgctgatgc ggtgctgatt   2580
acgaccgctc acgcgtggca gcatcagggg aaaaccttat ttatcagccg gaaaacctac   2640
cggattgatg gtagtggtca aatggcgatt accgttgatg ttgaagtggc gagcgataca   2700
ccgcatccgg cgcggattgg cctgaactgc cagctggcgc aggtagcaga gcgggtaaac   2760
tggctcggat tagggccgca agaaaactat cccgaccgcc ttactgccgc ctgttttgac   2820
cgctgggatc tgccattgtc agacatgtat ccccgtacg tcttcccgag cgaaaacggt   2880
ctgcgctgcg gaccgcgcga attgaattat ggcccacacc agtggcgcgg cgacttccag   2940
ttcaacatca gccgctacag tcaacagcaa ctgatggaaa ccagccatcg ccatctgctg   3000
cacgcggaag aaggcacatg gctgaatatc gacggtttcc atatgggat tggtggcgac   3060 gactcctgga gcccgtcagt atcggcggaa ttacagctga gcgccggtcg ctaccattac   3120
cagttggtct ggtgtcaaaa ataa                                         3144
```

<210> SEQ ID NO 2
<211> LENGTH: 1047

<212> TYPE: PRT
<213> ORGANISM: Escherichia coli

<400> SEQUENCE: 2

```
Met Ser Phe Thr Leu Thr Asn Lys Asn Val Ile Phe Val Ala Gly Leu
1               5                   10                  15

Gly Gly Ile Gly Leu Asp Thr Ser Lys Glu Leu Leu Lys Arg Asp Pro
            20                  25                  30

Val Val Leu Gln Arg Arg Asp Trp Glu Asn Pro Gly Val Thr Gln Leu
        35                  40                  45

Asn Arg Leu Ala Ala His Pro Pro Phe Ala Ser Trp Arg Asn Ser Glu
    50                  55                  60

Glu Ala Arg Thr Asp Arg Pro Ser Gln Gln Leu Arg Ser Leu Asn Gly
65                  70                  75                  80

Glu Trp Arg Phe Ala Trp Phe Pro Ala Pro Glu Ala Val Pro Glu Ser
                85                  90                  95

Trp Leu Glu Cys Asp Leu Pro Glu Ala Asp Thr Val Val Val Pro Ser
            100                 105                 110

Asn Trp Gln Met His Gly Tyr Asp Ala Pro Ile Tyr Thr Asn Val Thr
        115                 120                 125

Tyr Pro Ile Thr Val Asn Pro Pro Phe Val Pro Thr Glu Asn Pro Thr
    130                 135                 140

Gly Cys Tyr Ser Leu Thr Phe Asn Val Asp Glu Ser Trp Leu Gln Glu
145                 150                 155                 160

Gly Gln Thr Arg Ile Ile Phe Asp Gly Val Asn Ser Ala Phe His Leu
                165                 170                 175

Trp Cys Asn Gly Arg Trp Val Gly Tyr Gly Gln Asp Ser Arg Leu Pro
            180                 185                 190

Ser Glu Phe Asp Leu Ser Ala Phe Leu Arg Ala Gly Glu Asn Arg Leu
        195                 200                 205

Ala Val Met Val Leu Arg Trp Ser Asp Gly Ser Tyr Leu Glu Asp Gln
    210                 215                 220

Asp Met Trp Arg Met Ser Gly Ile Phe Arg Asp Val Ser Leu Leu His
225                 230                 235                 240

Lys Pro Thr Thr Gln Ile Ser Asp Phe His Val Ala Thr Arg Phe Asn
                245                 250                 255

Asp Asp Phe Ser Arg Ala Val Leu Glu Ala Glu Val Gln Met Cys Gly
            260                 265                 270

Glu Leu Arg Asp Tyr Leu Arg Val Thr Val Ser Leu Trp Gln Gly Glu
        275                 280                 285

Thr Gln Val Ala Ser Gly Thr Ala Pro Phe Gly Gly Glu Ile Ile Asp
    290                 295                 300

Glu Arg Gly Gly Tyr Ala Asp Arg Val Thr Leu Arg Leu Asn Val Glu
305                 310                 315                 320

Asn Pro Lys Leu Trp Ser Ala Glu Ile Pro Asn Leu Tyr Arg Ala Val
                325                 330                 335

Val Glu Leu His Thr Ala Asp Gly Thr Leu Ile Glu Ala Glu Ala Cys
            340                 345                 350

Asp Val Gly Phe Arg Glu Val Arg Ile Glu Asn Gly Leu Leu Leu Leu
        355                 360                 365

Asn Gly Lys Pro Leu Leu Ile Arg Gly Val Asn Arg His Glu His His
    370                 375                 380

Pro Leu His Gly Gln Val Met Asp Glu Gln Thr Met Val Gln Asp Ile
385                 390                 395                 400
```

```
Leu Leu Met Lys Gln Asn Asn Phe Asn Ala Val Arg Cys Ser His Tyr
            405                 410                 415
Pro Asn His Pro Leu Trp Tyr Thr Leu Cys Asp Arg Tyr Gly Leu Tyr
        420                 425                 430
Val Val Asp Glu Ala Asn Ile Glu Thr His Gly Met Val Pro Met Asn
            435                 440                 445
Arg Leu Thr Asp Asp Pro Arg Trp Leu Pro Ala Met Ser Glu Arg Val
        450                 455                 460
Thr Arg Met Val Gln Arg Asp Arg Asn His Pro Ser Val Ile Ile Trp
465                 470                 475                 480
Ser Leu Gly Asn Glu Ser Gly His Gly Ala Asn His Asp Ala Leu Tyr
                485                 490                 495
Arg Trp Ile Lys Ser Val Asp Pro Ser Arg Pro Val Gln Tyr Glu Gly
            500                 505                 510
Gly Gly Ala Asp Thr Thr Ala Thr Asp Ile Ile Cys Pro Met Tyr Ala
        515                 520                 525
Arg Val Asp Glu Asp Gln Pro Phe Pro Ala Val Pro Lys Trp Ser Ile
        530                 535                 540
Lys Lys Trp Leu Ser Leu Pro Gly Glu Thr Arg Pro Leu Ile Leu Cys
545                 550                 555                 560
Glu Tyr Ala His Ala Met Gly Asn Ser Leu Gly Gly Phe Ala Lys Tyr
                565                 570                 575
Trp Gln Ala Phe Arg Gln Tyr Pro Arg Leu Gln Gly Gly Phe Val Trp
                580                 585                 590
Asp Trp Val Asp Gln Ser Leu Ile Lys Tyr Asp Glu Asn Gly Asn Pro
                595                 600                 605
Trp Ser Ala Tyr Gly Gly Asp Phe Gly Asp Thr Pro Asn Asp Arg Gln
        610                 615                 620
Phe Cys Met Asn Gly Leu Val Phe Ala Asp Arg Thr Pro His Pro Ala
625                 630                 635                 640
Leu Thr Glu Ala Lys His Gln Gln Gln Phe Phe Gln Phe Arg Leu Ser
                645                 650                 655
Gly Gln Thr Ile Glu Val Thr Ser Glu Tyr Leu Phe Arg His Ser Asp
                660                 665                 670
Asn Glu Leu Leu His Trp Met Val Ala Leu Asp Gly Lys Pro Leu Ala
            675                 680                 685
Ser Gly Glu Val Pro Leu Asp Val Ala Pro Gln Gly Lys Gln Leu Ile
        690                 695                 700
Glu Leu Pro Glu Leu Pro Gln Pro Glu Ser Ala Gly Gln Leu Trp Leu
705                 710                 715                 720
Thr Val Arg Val Val Gln Pro Asn Ala Thr Ala Trp Ser Glu Ala Gly
                725                 730                 735
His Ile Ser Ala Trp Gln Gln Trp Arg Leu Ala Glu Asn Leu Ser Val
            740                 745                 750
Thr Leu Pro Ala Ala Ser His Ala Ile Pro His Leu Thr Thr Ser Glu
        755                 760                 765
Met Asp Phe Cys Ile Glu Leu Gly Asn Lys Arg Trp Gln Phe Asn Arg
        770                 775                 780
Gln Ser Gly Phe Leu Ser Gln Met Trp Ile Gly Asp Lys Lys Gln Leu
785                 790                 795                 800
Leu Thr Pro Leu Arg Asp Gln Phe Thr Arg Ala Pro Leu Asp Asn Asp
                805                 810                 815
```

```
Ile Gly Val Ser Glu Ala Thr Arg Ile Asp Pro Asn Ala Trp Val Glu
            820                 825                 830

Arg Trp Lys Ala Ala Gly His Tyr Gln Ala Glu Ala Ala Leu Leu Gln
        835                 840                 845

Cys Thr Ala Asp Thr Leu Ala Asp Ala Val Leu Ile Thr Thr Ala His
    850                 855                 860

Ala Trp Gln His Gln Gly Lys Thr Leu Phe Ile Ser Arg Lys Thr Tyr
865                 870                 875                 880

Arg Ile Asp Gly Ser Gly Gln Met Ala Ile Thr Val Asp Val Glu Val
                885                 890                 895

Ala Ser Asp Thr Pro His Pro Ala Arg Ile Gly Leu Asn Cys Gln Leu
            900                 905                 910

Ala Gln Val Ala Glu Arg Val Asn Trp Leu Gly Leu Gly Pro Gln Glu
        915                 920                 925

Asn Tyr Pro Asp Arg Leu Thr Ala Ala Cys Phe Asp Arg Trp Asp Leu
    930                 935                 940

Pro Leu Ser Asp Met Tyr Thr Pro Tyr Val Phe Pro Ser Glu Asn Gly
945                 950                 955                 960

Leu Arg Cys Gly Thr Arg Glu Leu Asn Tyr Gly Pro His Gln Trp Arg
                965                 970                 975

Gly Asp Phe Gln Phe Asn Ile Ser Arg Tyr Ser Gln Gln Gln Leu Met
            980                 985                 990

Glu Thr Ser His Arg His Leu Leu His Ala Glu Gly Thr Trp Leu
        995                 1000                1005

Asn Ile Asp Gly Phe His Met Gly Ile Gly Gly Asp Asp Ser Trp Ser
    1010                1015                1020

Pro Ser Val Ser Ala Glu Leu Gln Leu Ser Ala Gly Arg Tyr His Tyr
1025                1030                1035                1040

Gln Leu Val Trp Cys Gln Lys
                1045

<210> SEQ ID NO 3
<211> LENGTH: 925
<212> TYPE: PRT
<213> ORGANISM: Homo sapiens

<400> SEQUENCE: 3

Met Thr Thr Glu Gln Arg Arg Ser Leu Gln Ala Phe Gln Asp Tyr Ile
1               5                   10                  15

Arg Lys Thr Leu Asp Pro Thr Tyr Ile Leu Ser Tyr Met Ala Pro Trp
            20                  25                  30

Phe Arg Glu Glu Glu Val Gln Tyr Ile Gln Ala Glu Lys Asn Asn Lys
        35                  40                  45

Gly Pro Met Glu Ala Ala Thr Leu Phe Leu Lys Phe Leu Leu Glu Leu
    50                  55                  60

Gln Glu Glu Gly Trp Phe Arg Gly Phe Leu Asp Ala Leu Asp His Ala
65                  70                  75                  80

Gly Tyr Ser Gly Leu Tyr Glu Ala Ile Glu Ser Trp Asp Phe Lys Lys
                85                  90                  95

Ile Glu Lys Leu Glu Glu Tyr Arg Leu Leu Leu Lys Arg Leu Gln Pro
            100                 105                 110

Glu Phe Lys Thr Arg Ile Ile Pro Thr Asp Ile Ile Ser Asp Leu Ser
        115                 120                 125

Glu Cys Leu Ile Asn Gln Glu Cys Glu Glu Ile Leu Gln Ile Cys Ser
    130                 135                 140
```

-continued

```
Thr Lys Gly Met Met Ala Gly Ala Glu Lys Leu Val Glu Cys Leu Leu
145                 150                 155                 160

Arg Ser Asp Lys Glu Asn Trp Pro Lys Thr Leu Lys Leu Ala Leu Glu
                165                 170                 175

Lys Glu Arg Asn Lys Phe Ser Glu Leu Trp Ile Val Lys Gly Ile
                180                 185                 190

Lys Asp Val Glu Thr Glu Asp Leu Glu Asp Lys Met Glu Thr Ser Asp
                195                 200                 205

Ile Gln Ile Phe Tyr Gln Glu Asp Pro Glu Cys Gln Asn Leu Ser Glu
                210                 215                 220

Asn Ser Cys Pro Pro Ser Glu Val Ser Asp Thr Asn Leu Tyr Ser Pro
225                 230                 235                 240

Phe Lys Pro Arg Asn Tyr Gln Leu Glu Leu Ala Leu Pro Ala Met Lys
                245                 250                 255

Gly Lys Asn Thr Ile Ile Cys Ala Pro Thr Gly Cys Gly Lys Thr Phe
                260                 265                 270

Val Ser Leu Leu Ile Cys Glu His His Leu Lys Lys Phe Pro Gln Gly
                275                 280                 285

Gln Lys Gly Lys Val Val Phe Phe Ala Asn Gln Ile Pro Val Tyr Glu
                290                 295                 300

Gln Gln Lys Ser Val Phe Ser Lys Tyr Phe Glu Arg His Gly Tyr Arg
305                 310                 315                 320

Val Thr Gly Ile Ser Gly Ala Thr Ala Glu Asn Val Pro Val Glu Gln
                325                 330                 335

Ile Val Glu Asn Asn Asp Ile Ile Leu Thr Pro Gln Ile Leu Val
                340                 345                 350

Asn Asn Leu Lys Lys Gly Thr Ile Pro Ser Leu Ser Ile Phe Thr Leu
                355                 360                 365

Met Ile Phe Asp Glu Cys His Asn Thr Ser Lys Gln His Pro Tyr Asn
370                 375                 380

Met Ile Met Phe Asn Tyr Leu Asp Gln Lys Leu Gly Gly Ser Ser Gly
385                 390                 395                 400

Pro Leu Pro Gln Val Ile Gly Leu Thr Ala Ser Val Gly Val Gly Asp
                405                 410                 415

Ala Lys Asn Thr Asp Glu Ala Leu Asp Tyr Ile Cys Lys Leu Cys Ala
                420                 425                 430

Ser Leu Asp Ala Ser Val Ile Ala Thr Val Lys His Asn Leu Glu Glu
                435                 440                 445

Leu Glu Gln Val Val Tyr Lys Pro Gln Lys Phe Phe Arg Lys Val Glu
                450                 455                 460

Ser Arg Ile Ser Asp Lys Phe Lys Tyr Ile Ile Ala Gln Leu Met Arg
465                 470                 475                 480

Asp Thr Glu Ser Leu Ala Lys Arg Ile Cys Lys Asp Leu Glu Asn Leu
                485                 490                 495

Ser Gln Ile Gln Asn Arg Glu Phe Gly Thr Gln Lys Tyr Glu Gln Trp
                500                 505                 510

Ile Val Thr Val Gln Lys Ala Cys Met Val Phe Gln Met Pro Asp Lys
                515                 520                 525

Asp Glu Glu Ser Arg Ile Cys Lys Ala Leu Phe Leu Tyr Thr Ser His
                530                 535                 540

Leu Arg Lys Tyr Asn Asp Ala Leu Ile Ile Ser Glu His Ala Arg Met
545                 550                 555                 560
```

```
Lys Asp Ala Leu Asp Tyr Leu Lys Asp Phe Ser Asn Val Arg Ala
                565                 570                 575

Ala Gly Phe Glu Glu Ile Glu Gln Asp Leu Thr Gln Arg Phe Glu
            580                 585                 590

Lys Leu Gln Glu Leu Glu Ser Val Ser Arg Asp Pro Ser Asn Glu Asn
        595                 600                 605

Pro Lys Leu Glu Asp Leu Cys Phe Ile Leu Gln Glu Glu Tyr His Leu
    610                 615                 620

Asn Pro Glu Thr Ile Thr Ile Leu Phe Val Lys Thr Arg Ala Leu Val
625                 630                 635                 640

Asp Ala Leu Lys Asn Trp Ile Glu Gly Asn Pro Lys Leu Ser Phe Leu
                645                 650                 655

Lys Pro Gly Ile Leu Thr Gly Arg Gly Lys Thr Asn Gln Asn Thr Gly
            660                 665                 670

Met Thr Leu Pro Ala Gln Lys Cys Ile Leu Asp Ala Phe Lys Ala Ser
        675                 680                 685

Gly Asp His Asn Ile Leu Ile Ala Thr Ser Val Ala Asp Glu Gly Ile
    690                 695                 700

Asp Ile Ala Gln Cys Asn Leu Val Ile Leu Tyr Glu Tyr Val Gly Asn
705                 710                 715                 720

Val Ile Lys Met Ile Gln Thr Arg Gly Arg Gly Arg Ala Arg Gly Ser
                725                 730                 735

Lys Cys Phe Leu Leu Thr Ser Asn Ala Gly Val Ile Glu Lys Glu Gln
            740                 745                 750

Ile Asn Met Tyr Lys Glu Lys Met Met Asn Asp Ser Ile Leu Arg Leu
        755                 760                 765

Gln Thr Trp Asp Glu Ala Val Phe Arg Glu Lys Ile Leu His Ile Gln
    770                 775                 780

Thr His Glu Lys Phe Ile Arg Asp Ser Gln Glu Lys Pro Lys Pro Val
785                 790                 795                 800

Pro Asp Lys Glu Asn Lys Lys Leu Leu Cys Arg Lys Cys Lys Ala Leu
                805                 810                 815

Ala Cys Tyr Thr Ala Asp Val Arg Val Ile Glu Glu Cys His Tyr Thr
            820                 825                 830

Val Leu Gly Asp Ala Phe Lys Glu Cys Phe Val Ser Arg Pro His Pro
        835                 840                 845

Lys Pro Lys Gln Phe Ser Ser Phe Glu Lys Arg Ala Lys Ile Phe Cys
    850                 855                 860

Ala Arg Gln Asn Cys Ser His Asp Trp Gly Ile His Val Lys Tyr Lys
865                 870                 875                 880

Thr Phe Glu Ile Pro Val Ile Lys Ile Glu Ser Phe Val Val Glu Asp
                885                 890                 895

Ile Ala Thr Gly Val Gln Thr Leu Tyr Ser Lys Trp Lys Asp Phe His
            900                 905                 910

Phe Glu Lys Ile Pro Phe Asp Pro Ala Glu Met Ser Lys
        915                 920                 925

<210> SEQ ID NO 4
<211> LENGTH: 579
<212> TYPE: DNA
<213> ORGANISM: Mus musculus

<400> SEQUENCE: 4
atgggggtgc ccgaacgtcc caccctgctg cttttactct ccttgctact gattcctctg    60
```

```
ggcctcccag tcctctgtgc tcccccacgc ctcatctgcg acagtcgagt tctggagagg    120
tacatcttag aggccaagga ggcagaaaat gtcacgatgg gttgtgcaga aggtcccaga    180
ctgagtgaaa atattacagt cccagatacc aaagtcaact tctatgcttg aaaagaatg    240 gaggtggaag aacaggccat agaagtttgg caaggcctgt ccctgctctc agaagccatc    300
ctgcaggccc aggccctgct agccaattcc tcccagccac cagagaccct tcagcttcat    360
atagacaaag ccatcagtgg tctacgtagc ctcacttcac tgcttcgggt actgggagct    420
cagaaggaat tgatgtcgcc tccagatacc accccacctg ctccactccg aacactcaca    480
gtggatactt tctgcaagct cttccgggtc tacgccaact tcctccgggg gaaactgaag    540
ctgtacacgg gagaggtctg caggagaggg gacaggtga                          579

<210> SEQ ID NO 5
<211> LENGTH: 1897
<212> TYPE: DNA
<213> ORGANISM: Photinus pyralis

<400> SEQUENCE: 5
atgcacatat cgaggtgaac atcacgtacg cggaatactt cgaaatgtcc gttcggttgg     60
cagaagctat gaaacgatat gggctgaata caaatcacag aatcgtcgta tgcagtgaaa    120
actctcttca attctttatg ccggtgttgg gcgcgttatt tatcggagtt gcagttgcgc    180
ccgcgaacga catttataat gaacgtaagc accctcgcca tcagaccaaa gggaatgacg    240
tatttaattt ttaaggtgaa ttgctcaaca gtatgaacat tcgcagcct accgtagtgt    300 ttgtttccaa aaaggggttg caaaaaattt gaacgtgca aaaaaaatta ccaataatcc    360
agaaaattat tatcatggat tctaaaacgg attaccaggg atttcagtcg atgtacacgt    420
tcgtcacatc tcatctacct cccggtttta atgaatacga ttttgtacca gagtcctttg    480
atcgtgacaa acaattgca ctgataatga attcctctgg atctactggg ttacctaagg    540
gtgtggccct tccgcataga actgcctgcg tcagattctc gcatgccagg tatgtcgtat    600
aacaagagat taagtaatgt tgctacacac attgtagaga tcctattttt ggcaatcaaa    660
tcattccgga tactgcgatt ttaagtgttg ttccattcca tcacggtttt ggaatgttta    720
ctacactcgg atatttgata tgtggatttc gagtcgtctt aatgtataga tttgaagaag    780
agctgttttt acgatccctt caggattaca aaattcaaag tgcgttgcta gtaccaaccc    840 tatttcatt cttcgccaaa agcactctga ttgacaaata cgatttatct aatttacacg    900
aaattgcttc tgggggcgca cctctttcga agaagtcgg ggaagcggtt gcaaacggt    960 gagttaagcg cattgctagt atttcaaggc tctaaaacgg cgcgtagctt ccatcttcca   1020
gggatacgac aaggatatgg gctcactgag actacatcag ctattctgat tacacccgag   1080
ggggatgata aaccgggcgc ggtcggtaaa gttgttccat tttttgaagc gaaggttgtg   1140 gatctgata ccgggaaaac gctgggcgtt aatcagagag gcgaattatg tgtcagagga    1200
cctatgatta tgtccggtta tgtaaacaat ccggaagcga ccaacgcctt gattgacaag   1260
gatggatggc tacattctgg agacatagct tactgggacg aagacgaaca cttcttcata   1320
gttgaccgct tgaagtcttt aattaaatac aaaggatatc aggtaatgaa gattttttaca   1380 tgcacacacg ctacaatacc gtaggtggc cccgctgaa ttggaatcga tattgttaca    1440
acaccccaac atcttcgacg cgggcgtggc aggtcttccc gacgatgacg ccggtgaact   1500
tcccgccgcc gttgttgttt tggagcacgg aaagacgatg acggaaaaag agatcgtgga   1560
ttacgtcgcc agtaaatgaa ttcgttttac gttactcgta ctacaattct tttcataggt    1620
```

```
caagtaacaa ccgcgaaaaa gttgcgcgga ggagttgtgt ttgtggacga agtaccgaaa    1680
ggtcttaccg gaaaactcga cgcaagaaaa atcagagaga tcctcataaa ggccaagaag    1740
ggcggaaagt ccaaattgta aaatgtaact gtattcagcg atgacgaaat tcttagctat    1800
tgtaatatta tatgcaaatt gatgaatggt aattttgtaa ttgtgggtca ctgtactatt    1860
ttaacgaata ataaaatcag gtataggtaa ctaaaaa                             1897
```

CAPPED AND UNCAPPED RNA MOLECULES AND BLOCK COPOLYMERS FOR INTRACELLULAR DELIVERY OF RNA

CROSS-REFERENCE TO RELATED APPLICATIONS

This application is a U.S. National Stage Application pursuant to 35 U.S.C. § 371 of International Patent Application PCT/IB2015/052405, filed on Apr. 1, 2015, and published as WO 2015/151048 on Oct. 8, 2015, which claims priority to European Patent Application 14305472.4, filed on Apr. 1, 2014, all of which are incorporated herein by reference in their entireties for all purposes.

FIELD OF THE INVENTION

The instant invention relates to the field of gene therapy, and more particularly to the vectorisation of RNA molecules such as messenger RNAs (mRNA). In particular, the invention relates to the use of a tetrafunctional non-ionic amphiphilic block copolymer as a vehicle for mRNAs.

More specifically, the invention relates to the vectorisation of capped and uncapped mRNAs by tetrafunctional non-ionic amphiphilic block copolymers.

BACKGROUND OF THE INVENTION

The instant invention relates to the field of gene therapy, and more particularly to the vectorisation of RNA molecules such as messenger RNAs (mRNA). In particular, the invention relates to the use of a tetrafunctional non-ionic amphiphilic block copolymer as a vehicle for messenger RNAs.

Different strategies have been proposed in the Art for the intracellular delivery of compounds, and more particularly of RNA molecules.

In particular, numerous non-viral cationic vectors or cationic transfection agents have been synthesized and are currently used for delivery of nucleic acids into cultured cells. The principle of non-viral gene delivery relies on the interaction of nucleic acids with cationic residues present on the vector through electrostatic forces.

WO2003018603A1 relates to aminoglycoside lipid derivatives for transfection. This document teaches the use of lipoaminoglycosides as nanocarriers for nucleic acid delivery. Such lipoaminoglycosides are generally composed of a polar head which is an aminoglycoside, of one spacer and of an hydrophobic tail which may be composed of dioleyl chains and/or cholesterol. Examples of such transfection reagents include DOSP, DOST, DOSK, DOSN, CHOLP, CHOLT, CHOLK and CHOLN. Those transfection reagents tend to form lamellar complexes. Although they have proven to be useful as transfection reagents in vitro, they also tend to be less efficient in vivo or in situ.

WO2010026537A1 relates to stabilized multimodular self-assemblies for intracellular delivery, which are composed of at least one cationic transfection agent, of at least one negatively charged macromolecule, and of at least one amphiphilic block copolymer acting as a steric colloidal stabilizer.

More recently, glycosylated tetrafunctional non-ionic amphiphilic block copolymers have also been reported as immune adjuvants in WO2013128423A1.

However the transfection of RNA molecules, and more particularly messenger RNAs, does not always lead to in vivo satisfactory protein production, which may be due in part to poor transfection efficiency and/or lack of stability of the transfected RNA molecules once they have been internalized.

What is more, those systems have mostly been used so far for nucleic acids of the DNA type.

Thus there is still a need for novel transfection reagents with respect to RNA molecules, and with a good safety profile suitable for human use and therapy.

There is also a need for novel methods for improving intracellular delivery, and more specifically gene therapy and/or gene silencing.

In particular, there remains a need for providing methods and reagents which allow not only efficient intracellular delivery of a nucleic acid, such as messenger RNA, but which may further provide efficient protein expression in vivo and/or a controlled immune response.

There is also a need for novel strategies for transfecting RNA molecules into an host, which may further provide long-lasting effects in the context of gene therapy and/or gene silencing.

The instant invention has for object to meet those needs.

Thus, a first object of the invention relates to the use of at least one tetrafunctional non-ionic amphiphilic block copolymer, as a vehicle for capped or uncapped mRNAs for intracellular delivery for gene therapy.

In particular, the inventors have unexpectedly observed, as detailed in the examples below, that the combination of (i) uncapped RNA molecules, and more particularly uncapped mRNAs, with (ii) block copolymers of the invention led to in vivo protein expression.

They have also observed that messenger RNA molecules transfected with a block copolymer of the invention as a vehicle led to in vivo transfection efficiency, coupled with almost no induction of specific immune reaction.

Thus, the inventors now show herein that the specific combination of RNA molecules, such as mRNAs, with block copolymers of the invention is particularly efficient for intracellular delivery for gene therapy.

This result was unexpected because it is known in the Art that primary RNA transcripts have to go through multiple co-transcriptional modifications in order to be converted into a mature RNA. In particular, it has been known for years that the so-called "Capping" step of pre-mature RNA transcripts is essential for efficient gene expression and RNA stability (see Hocine et al.; "RNA Processing and Export"; Cold Spring Harb Perspect Biol.; 2010. See also Schoenberg et al.; "Re-capping the message"; Trends Biochem Sci.; 2009).

Even more surprisingly, it is now shown that by transfecting an RNA molecule with a block copolymer of the invention as a vehicle, said transfection does not trigger, or at least in a very-limited way, nons-elf recognition and/or innate immune stimulation and antiviral innate immunity.

RIG-I (of sequence SEQ ID N°4) was initially reported as a retinoic acid-inducible gene in 1997 (GenBank: AF038963) and belongs to the Pattern-Recognition Receptor (PRR) family. It is also known to trigger type 1 interferon expression upon detection of viral RNA.

Without wishing to be hound by the theory, it is believed that the combination of the invention does not trigger any RIG-I dependent-response, or at least in a very-limited way, which thus results in higher stability of the transfected RNA molecules.

This other result was also unexpected, as it is known in the Art that the RIG-I (retinoic acid-inducible gene I) receptor, which is heavily involved in innate immunity recognition of exogenous (non-host) RNA molecules, such as RNAs of viral origin, is known to interact specifically with uncapped RNA molecules (see Kolakofsky et al.; "A structure-based model of RIG-I activation"; RNA; 2012).

Even more surprisingly, it is shown herein that, uncapped or capped, and modified RNA molecules such as mRNAs, are also efficient for intracellular delivery and for triggering in vivo protein expression in combination with a block polymer of the invention.

In particular, it is also shown herein that the combination of (i) uncapped modified or uncapped unmodified RNA molecules and of (ii) block copolymers of the invention as a vehicle are a particularly efficient combination, and a promising tool not only for intracellular delivery for gene therapy.

Without wishing to be bound by the theory, it is believed that this combination is also efficient for abrogating RNA interaction with Toll-like receptors such as TLR3, TLR7 and TLR8 (see Kormann et al.; "Expression of therapeutic proteins after delivery of chemically modified mRNA in mice"; Nature Biotechnology; 2010).

In other words, it is believed that the specific combination of (i) RNA molecules and (ii) block copolymers of the invention provides efficient intracellular delivery, as well as decreased activation of the immune system, presumably due to surprisingly reduced binding in vivo to pattern recognition receptors.

In particular, it is proposed that a surprisingly reduced activation of RIG-I dependent and Toll-like receptors (TLRs) dependent pathways in vivo may both account for the synergistic effect of (i) uncapped mRNAs and (ii) block copolymers of the invention on in vivo protein expression efficiency (Katze et al.; "Innate immune modulation by RNA viruses: emerging insights from functional genomics"; Nature Reviews Immunology; 2008). An amino acid sequence or RIG-I (SEQ ID N° 3) is provided herein solely for reference.

As shown from the examples, this surprisingly high in vivo protein expression efficiency is specific to nanocarriers which involve block copolymers of the invention, such as the tetrafunctional block copolymer 704, as vehicles.

The decreased activation of the immune system corresponding to the transfection of a given nucleic acid into an eukaryotic cell may be assessed using either one of the protocols which have been described in the Material & Methods section, relating to EPO or β-galactosidase.

This decreased activation may correspond to a decreased type-I or humoral immune response associated with both:
(i) a low or moderate variation of the percentage of CD8+IFNγ+ cells among total splenic CD8+ cells; and/or
(ii) a low or moderate production of antibodies directed towards the recombinant protein encoded by the transfected RNA molecule.

Furthermore, the inventors have unexpectedly discovered that the efficiency of expression is observed even with low concentrations of block copolymer of the invention. Thus, block copolymer can be used at a concentration as low as $20.10^{-4}\%$ (w/v) which is a 75 fold lower concentration than that used for optimal in vivo delivery of DNA.

The efficiency of expression may be assessed based on the level of expression of a given protein after administration of block copolymers of the invention in combination with a messenger RNA suitable for expression of the said protein. The level of expression is then compared to a reference value determined after administration of naked mRNA (without the said block copolymer).

Because the amount of block copolymer that is administered with the mRNA may have an impact on the level of expression of a protein, the efficiency of expression may also be assessed as a ratio between the level of expression of the said protein and the amount that is administered (i.e. expressed as a weight percentage compared to the total volume of a given dose).

Methods for determining the level of expression are further detailed in the Material & Methods section, in particular for β-gal, EPO and luciferase expression.

For example, the efficiency of expression for a given block copolymer may be assessed in vivo on mice by:
(i) administering to mice, preferably intramuscularly, a given block copolymer in combination with a mRNA encoding the said β-gal, EPO and/or luciferase;
(ii) measuring the level of expression of the said β-gal, EPO and/or luciferase in the said mice;
(iii) comparing the level of expression measured at step (ii) to a reference value, or alternatively comparing the ratio between the said level of expression and the amount that was administered to a reference value.

According to exemplary embodiments, the block copolymer is administered at a concentration as low as $20.10^{-4}\%$ (w/v).

According to said exemplary embodiment, the block copolymer may be administered on mice at a volume of about 50 μL.

Also, and in a general manner, the increase of expression for a given mRNA does not necessarily follow strictly the increase of the amount of its corresponding "carrier", and with a linear relation; in other words, there is not necessarily a strict correlation between those two values, which may thus lead to a phenomenon of saturation, or alternatively inadequate or delayed expression of a given protein in the eukaryotic host.

On the other hand, the inventors have also unexpectedly discovered that the maximal efficiency of expression can also be increased significantly (see FIGS. 7 and 8), even at high concentrations.

Thus, the block copolymers of the invention, when in combination with RNA molecules, as vehicles, are particularly efficient for intracellular delivery and gene therapy due to:
(i) high efficiency of expression even when used in low amounts;
(ii) maximal efficiency of expression;
(iii) low immunogenicity.

According to one of its aspects, the invention relates to at least one tetrafunctional non-ionic amphiphilic block copolymer, as a vehicle for at least one RNA molecule and in particular at least one capped or uncapped mRNA, either as such or for use for intracellular delivery.

According to another of its aspects, the invention relates to a pharmaceutical composition and/or a transfection reagent comprising at last one tetrafunctional non-ionic amphiphilic block copolymer, as a vehicle for at least one RNA molecule and in particular at least one capped or uncapped mRNA.

According to another of its aspects, the invention relates to a therapeutic and/or non-therapeutic method for increasing, improving, or maintaining the expression of a protein in an eukaryotic host, which comprises a step of transfecting into said host at least one tetrafunctional non-ionic amphiphilic block copolymer, as a vehicle for at least one RNA molecule and in particular at least one capped or uncapped mRNA, suitable for encoding said protein within said host.

According to the invention, an "eukaryotic host" may encompass any human or non-human mammal, as well as any in vitro or ex vivo sample, such as a cell or tissue sample.

Methods and reagents of the invention are also suitable for gene therapy. Thus, it is clear that the invention further relates to a combination of (i) at least one block copolymer, in a particular at least one tetrafunctional non-ionic amphiphilic block copolymer, and (ii) at least one RNA molecule such as a mRNA, for use for intracellular delivery, and in the context of gene therapy.

For gene therapy, block copolymers of the invention may serve as a vehicle for at least one RNA molecule and in particular one messenger RNA such as an uncapped messenger RNA.

According to another of its aspects, the invention relates to the use of at least one tetrafunctional non-ionic amphiphilic block copolymer, as a vehicle for at least one RNA molecule and in particular at least one uncapped RNA molecule for the manufacture of a medicament intended to be used for intracellular delivery for gene therapy.

According to the invention, "comprising" also includes "consisting of".

RNA Molecules

These may be sequences of natural or artificial origin, and in particular mRNA (messenger RNA), tRNA (transfer RNA), rRNA (ribosomal RNA), siRNA (silencing RNA), miRNA (micro RNA), mtRNA (mitochondrial RNA), shRNA (short hairpin RNA), tmRNA (transfer-messenger RNA), vRNA (viral RNA), single-stranded, double-stranded and/or base-paired RNA (ssRNA; dsRNA and bpRNA respectively), blunt-ended RNA or not, mature and immature mRNAs, coding and non-coding RNAs, hybrid sequences or synthetic or semisynthetic sequences of oligonucleotides, modified or otherwise, and mixtures thereof.

Accordingly, these may be messenger RNAs (mRNA), which includes mature and immature mRNAs, such as precursor mRNAs (pre-mRNA) or heterogeneous nuclear mRNAs (hnRNA) and mature mRNAs. Thus, RNA molecules of the invention also encompass monocistronic and polycistronic messenger RNAs.

For the sake of clarity, a mRNA encompasses any coding RNA molecule, which may be translated by an eukaryotic host into a protein.

A coding RNA molecule generally refers to a RNA molecule comprising a sequence coding for a protein of interest and which may be translated by the eukaryotic host, said sequence starting with a start codon (ATG) and preferably terminated by a stop codon (i.e. TAA, TAG, TGA).

According to a general embodiment, a mRNA of the invention comprises or consists of the following general formula:

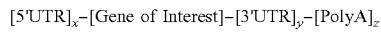

[5'UTR]$_x$-[Gene of Interest]-[3'UTR]$_y$-[PolyA]$_z$ wherein [5'UTR] and [3'UTR] are untranslated regions (UTR),
wherein [5'UTR] contains a Kozak sequence,
wherein [Gene of Interest] is any gene coding for a protein of interest,
wherein [PolyA] is a poly(A) tail, and
wherein x, y, and z, are identical or different, and equal to 0 or 1.

Preferably, a mRNA of the invention consists of the following general formula:

[5'UTR]-[Gene of Interest]-[3'UTR]-[PolyA]

wherein [5'UTR] and [3'UTR] are untranslated regions,
wherein [5'UTR] contains a Kozak sequence,
wherein [Gene of Interest] is any nucleic acid coding for a protein of interest, and
wherein [PolyA] is a poly(A) tail.

It is reminded that a Kozak sequence refers to a sequence, which is generally a consensus sequence, occurring on eukaryotic mRNAs and which plays a major role in the initiation of the translation process. Kozak sequences and Kozak consensus sequences are well known in the Art.

It is also reminded that a poly(A) tail consists of multiple adenosine monophosphates that is well known in the Art. A poly(A) tail is generally produced during a step called polyadenylation that is one of the post-translation modifications which generally occur during the production of mature messenger RNAs; such poly(A) tail contribute to the stability and the half-life of said mRNAs, and can be of variable length.

In particular, a poly(A) tail may be equal or longer than 10 A nucleotides, which includes equal or longer than 20 A nucleotides, which includes equal or longer than 100 A nucleotides, and for example about 120 A nucleotides.

The [3'UTR] does not express any proteins. The purpose of the [3'UTR] is to increase the stability of the mRNA. According to a particular embodiment, the α-globin UTR is chosen because it is known to be devoid of instability.

Advantageously, the sequence corresponding to the gene of interest may be codon-optimized in order to obtain a satisfactory protein production within the host which is considered.

RNA molecules of the invention may be of variable length. Thus, they may be short RNA molecules, for instance RNA molecules shorter than about 100 nucleotides, or long RNA molecules, for instance longer than about 100 nucleotides, or even longer than about 300 nucleotides.

According to exemplary embodiments, the gene of interest may code for a reporter protein, such as Luciferase or β-galactosidase. The nucleic acid sequence of Luciferase (SEQ ID N° 5) is solely provided herein for reference. The nucleic acid sequence of β-galactosidase (SEQ ID N° 1) and the amino acid sequence of β-galactosidase (SEQ ID N°2) are solely provided herein for reference.

These nucleic acids may be of eukaryotic or procaryotic origin, and more particularly of human, animal, plant, bacterial, yeast or viral origin and the like. They may be obtained by any technique known to persons skilled in the art, and in particular by screening libraries, by chemical synthesis or alternatively by mixed methods including chemical or enzymatic modification of sequences obtained by screening libraries. They may be chemically modified.

Thus, RNA molecules of the invention, such as mRNAs, may encompass synthetic or artificial RNA molecules, but also naturally-occurring RNA molecules.

According to the invention, a RNA molecule, such as a messenger RNA (or mRNA), encompasses the following species:
(i) capped unmodified RNA molecule;
(ii) capped modified RNA molecule;
(iii) uncapped unmodified RNA molecule;
(iv) uncapped modified RNA molecule.

The above-mentioned terms are further detailed herebelow.

Capped and Uncapped RNA Molecules

According to a most general embodiment, a "capped RNA molecule" refers to a RNA molecule of which the 5' end is linked to a guanosine or a modified guanosine, preferably a 7-methylguanosine (m$^7$G), connected to a 5' to 5' triphosphate linkage or analog. This definition is commensurate with the most widely-accepted definition of a 5' cap, in particular of a naturally-occurring and/or physiological cap.

In the sense of the invention, "cap analogs" include caps which are biologically equivalent to a 7-methylguanosine (m⁷G), connected to a 5' to 5' triphosphate linkage, and which can thus be also substituted without impairing the protein expression of the corresponding messenger RNA in the eukaryotic host.

Thus, an "uncapped RNA molecule" refers to any RNA molecule that does not belong to the definition of a "capped RNA molecule".

Thus, according to a general and preferred embodiment, an "uncapped mRNA" may refer to a mRNA of which the 5' end is not linked to a 7-methylguanosine, through a 5' to 5' triphosphate linkage, or an analog as previously defined.

phate, 3'-phosphate, 3'phosphorothioate, phosphorodithioate, or bridging or non-bridging methylphosphonate moiety.

Other examples of synthetic caps or cap analogs include ARCA cap analogs, N1-methyl-guanosine, 2'-fluoro-guanosine, 7-deaza-guanosine, 8-oxo-guanosine, 2-amino-guanosine, LNA-guanosine, and 2-azido-guanosine.

Of note, among synthetic caps, some of the above-mentioned caps are suitable as analogs, but not others which may on the contrary hinder protein expression. Such distinction is understood by the man skilled in the Art.

For reference, and in a non-limitative manner, the structure of an Anti Reverse Cap Analog (ARCA) 3'-O-Me-m⁷G (5')ppp(5')G Cap analog is presented herebelow:

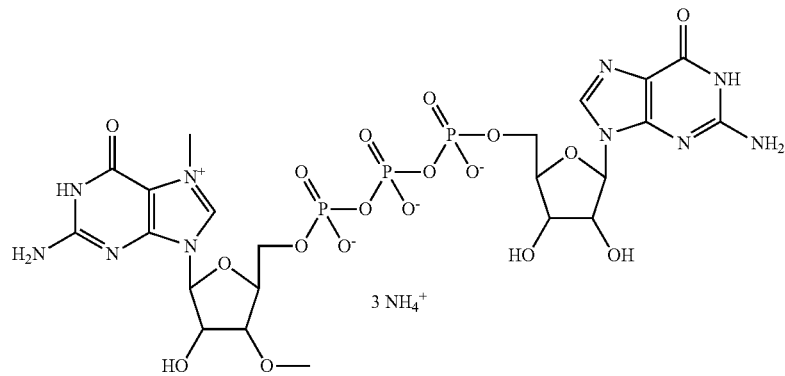 [SMILES: COC1C(COP(=O)([O-])OP(=O)([O-])OP(=O)([O-])OCC2OC(n3cnc4c(=O)[nH]c(N)nc43)C(O)C2O)OC(n2c[n+](C)c3c(=O)[nH]c(N)nc32)C1O]

An uncapped RNA molecule, such as a messenger RNA, may be an uncapped RNA molecule having a (5')ppp(5'), a (5')pp(5'), a (5')p(5') or even a (5')OH extremity. Such RNA molecules may be respectively abbreviated as $_{5'ppp}$RNA; $_{5'pp}$RNA; $_{5'p}$RNA; $_{5'OH}$RNA. Preferably, an uncapped RNA molecule of the invention is a messenger $_{5'ppp}$RNA.

Thus, when the RNA molecule is a single-stranded RNA molecule, it may be respectively abbreviated as $_{5'ppp}$ssRNA; $_{5'pp}$ssRNA; $_{5'p}$ssRNA; $_{5'OH}$ssRNA.

Thus, when the RNA molecule is a double-stranded RNA molecule, it may be respectively abbreviated as $_{5'ppp}$dsRNA; $_{5'pp}$dsRNA; $_{5'p}$dsRNA; $_{5'OH}$dsRNA.

Preferably, an uncapped mRNA of the invention is an uncapped single-stranded mRNA.

According to an even more preferred embodiment, an uncapped single-stranded mRNA may be an uncapped messenger $_{5'ppp}$ssRNA.

In a non-limitative manner, the first base of said uncapped RNA molecule may be either an adenosine, a guanosine, a cytosine, or an uridine.

Thus, an uncapped RNA molecule may be an uncapped RNA molecule having a (5')ppp(5'), a (5')pp(5'), a (5')p(5') or even a blunt-ended 5' guanosine extremity.

Examples of synthetic caps and/or cap analogs can be selected in a list consisting of: glyceryl, inverted deoxy abasic residue (moiety), 4', 5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threopentofuranos 1 nucleotide, acyclic 3', 4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phos- The ARCA cap analog is, for instance, an example of cap analog used during in vitro transcription: it is a modified cap in which the 3'OH group (closer to m⁷G) is replaced with —OCH₃. However, 100% of the transcripts synthesized with ARCA at the 5' end are translatable leading to a strong stimulatory effect on translation.

According to the invention, the "activation of PRR(s)" is understood as the stimulation, upon binding to the said PRR(s), of innate immunity, and more particularly of the expression of type 1 interferons.

According to said embodiment, a requirement for RIG-I activation may be a blunt-ended base-paired RNA (bpRNA), 10-20 bp long with a 5'triphosphate and free of mismatches near the blunt end.

According to another embodiment, a requirement for RIG-I activation may be a short, blunt-ended $_{5'OH}$bpRNA (see Kolakofsky et al.; "A structure-based model of RIG-I activation"; RNA; 2012).

Modified and Unmodified RNA Molecules

Within the invention, a "modified RNA molecule". refers to a RNA molecule which contains at least one modified nucleotide, nucleoside or base, such as a modified purine or a modified pyrimidine. A modified nucleoside or base can be any nucleoside or base that is not A, U, C or G (respectively Adenosine, Uridine, Cytidine or Guanosine for nucleosides; and Adenine, Uracil, Cytosine or Guanine when referring solely to the sugar moiety).

According to the invention, the expression "at least one . . . " such as in "at least one modified base" should be understood as having one or more modified bases. Thus, in this context, such term may encompass any RNA molecule having two or more modified bases, or even only modified bases.

Accordingly, an "unmodified RNA molecule" refers to any RNA molecule that is NOT commensurate with the definition of a modified RNA molecule.

In the sense of the invention, the terms "modified and unmodified" are considered distinctly from the terms "capped and uncapped", as the latter specifically relates to the base at the 5'-end of a RNA molecule in the sense of the invention.

According to the most preferred embodiment, a "modified RNA molecule". refers to a RNA molecule, such as a mRNA, which contains at least one base or sugar modification as described above, and preferably at least one base modification as described above.

In a non-limitative manner, examples of modified nucleotides, nucleosides and bases are disclosed in WO2015024667A1.

Thus, a modified RNA molecule may contain modified nucleotides, nucleosides or bases, including backbone modifications, sugar modifications or base modifications.

A backbone modification in connection with the present invention includes modifications, in which phosphates of the backbone of the nucleotides contained in a RNA molecule as defined herein are chemically modified A sugar modification in connection with the present invention includes chemical modifications of the sugar of the nucleotides of the RNA molecule as defined herein.

A base modification in connection with the present invention includes chemical modifications of the base moiety of the nucleotides of the RNA. In this context nucleotide analogues or modifications are preferably selected from nucleotide analogues which are suitable for transcription and/or translation of the RNA molecule in an eukaryotic cell.

Sugar modifications may consist in replacement or modification of the 2' hydroxy (OH) group, which can be modified or replaced with a number of different "oxy" or "deoxy" substituents.

Examples of "oxy"-2 ' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O) nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH$_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O The sugar group can also contain one or more carbons that possess the opposite stereochemical configuration than that of the corresponding carbon in ribose. Thus, a modified RNA can include nucleotides containing, for instance, arabinose as the sugar.

The phosphate backbone may further be modified and incorporated into the modified RNA molecule, as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein.

Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

The modified nucleosides and nucleotides, which may be incorporated into the modified RNA molecule, as described herein, can further be modified in the nucleobase moietyFor example, the nucleosides and nucleotides described herein can be chemically modified on the major groove face. In some embodiments, the major groove chemical modifications can include an amino group, a thiol group, an alkyl group, or a halo group.

For examples, the nucleotide analogues/modifications are selected from base modifications selected in a list consisting of: 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-0-Methyl inosine-5'-triphosphate 4-thiouridine-5'-triphosphate, 5-aminoallylcytidine-5'-triphosphate, 5-aminoallyluridine-5'-triphosphate, 5-bromocytidine-5 '-triphosphate, 5-bromouridine-5 '-triphosphate, 5-Bromo-2'-deoxycytidine-5 '-triphosphate, 5-Bromo-2'-deoxyuridine-5 '-triphosphate, 5-iodocytidine-5'-triphosphate, 5-lodo-2'-deoxycytidine-5'-triphosphate, 5-iodouridine-5'-triphosphate, 5-lodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5 '-triphosphate, 6-azacytidine-5 '-triphosphate, 6-azauridine-5 '-triphosphate, 6-chloropurineriboside-5'-triphosphate, 7-deazaadenosine-5'-triphosphate, 7-deazaguanosine-5'-triphosphate, 8-azaadenosine-5 '-triphosphate, 8-azidoadenosine-5 '-triphosphate, benzimidazole-riboside-5 '-triphosphate, N1-methyl adenosine-5'-triphosphate, N1-methylguanosine-5'-triphosphate, N6-methyladenosine-5'-triphosphate, 06-methylguanosine-5 '-triphosphate, pseudouridine-5 '-triphosphate, or puromycin-5'-triphosphate, xanthosine-5'-triphosphate.

In some embodiments, modified nucleosides may be selected from a list consisting of: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine; 4-methoxy-pseudouridine, and 4-methoxy-2-thio-pseudouridine.

In some embodiments, modified nucleosides and nucleotides include 5-aza-cytidine, pseudoisocytidine, 3-methylcytidine, N4-acetylcytidine, 5-foiniylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio- 1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2- thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2, 6-diaminopurine, 7-deaza-8-aza-2, 6-diaminopurine, 1-methyladenosine, N6-methyladenosine, N6-isopentenyl adenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methyl guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

According to a further embodiment, the modified RNA as defined herein can contain a lipid modification.

Modified bases and/or modified RNA molecules are known in the Art and are, for instance, further taught in Warren et al. ("Highly Efficient Reprogramming to Pluripotency and Directed Differentiation of Human Cells with Synthetic Modified mRNA"; Cell Stem Cell; 2010).

In view of the above, a modified base may be a modified purine base or a modified pyrimidine base.

In a non-limitative manner, examples of modified purine bases include modified adenosine and/or modified guanosine, such as hypoxanthine; xanthine; 7-methylguanine; inosine; xanthosine and 7-methylguanosine.

According to some embodiments, a modified RNA molecule or mRNA corresponds to a RNA for which each nucleoside corresponding to either Uridine, Cytidine, Adenosine and/or Ribothymidine is modified.

In a non-limitative manner, examples of modified pyrimidine bases include modified cytidine and/or modified uridine, such as 5,6-dihydrouracil; pseudouridine; 5-methylcytidine; 5-hydroxymethylcytidine; dihydrouridine and 5-methylcytidine.

Preferably, a modified base of the invention may be a modified uridine or cytidine, such a pseudouridine and 5-methylcytidine.

According to some embodiments, a modified RNA molecule or mRNA corresponds to a RNA for which each base corresponding to either U (for Uracile), C (for Cytosine), A (for Adenine) and/or T (for Thymine) is modified.

According to some exemplary embodiments, a modified RNA molecule or mRNA corresponds to a RNA for which each base corresponding to U (for Uracile) and C (for Cytosine) is modified.

For reference a structure of Pseudouridine-5'-Triphosphate, or Pseudo-UTP, or 5-Ribosyl Uracil is presented herebelow:

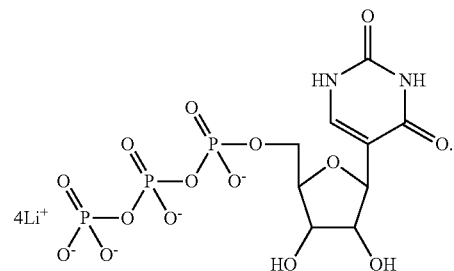 [SMILES: O=c1[nH]cc(C2OC(COP(=O)([O-])OP(=O)([O-])OP(=O)([O-])[O-])C(O)C2O)c(=O)[nH]1]

For reference a structure of 5-Methylcytidine-5'-Triphosphate, or 5-Methyl-CTP, or 5-Me-CTP, is presented herebelow:

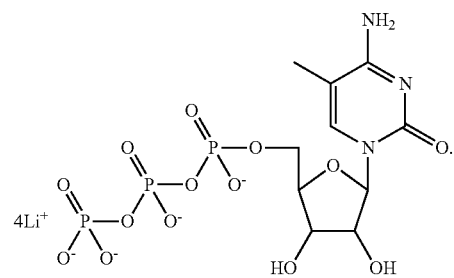 [SMILES: Cc1cn(C2OC(COP(=O)([O-])OP(=O)([O-])OP(=O)([O-])[O-])C(O)C2O)c(=O)nc1N]

Capped and uncapped mRNAs, whether modified or unmodified, may also be obtained commercially.

In a non-limitative manner, mRNAs which have been described herein may be ordered from TriLink Biotechnologies, Inc., and selected in the list consisting of:

L-6309 β-gal mRNA unmodified ARCA cap (Batch #T1-APG01A)

L-6109 β-gal mRNA fully substituted with Pseudo-U and 5-Methyl-C, ARCA cap (Batch #T1-AOL03A)

L-6309 β-gal mRNA unmodified, NO Cap (Batch #I9-B01A)

L-6109 β-gal mRNA fully substituted with Pseudo-U and 5-Methyl-C, No Cap (Batch #I9-B02A)

L-6007 Flue mRNA unmodified ARCA cap (I99-A01A), and

L-6007 EPO mRNA unmodified ARCA cap (I9-A01A).

A nucleic acid encoding EPO (SEQ ID N° 4) is provided herein solely for reference.

It is understood that an uncapped RNA molecule may be either a modified RNA molecule or an unmodified RNA molecule.

Accordingly, a capped RNA molecule may be either a modified RNA molecule or an unmodified RNA molecule.

Preferably, a RNA molecule of the invention is a messenger RNA (mRNA).

An RNA molecule of the invention is preferably an uncapped messenger RNA, either in a modified or in an unmodified form.

According to a most preferred embodiment, an uncapped mRNA is an uncapped unmodified mRNA or an uncapped modified mRNA.

In a non-limitative manner, an uncapped RNA molecule, such as a messenger RNA may also be an uncapped RNA molecule having only naturally-occurring bases.

According to the invention, a "naturally-occurring base" relates to a base that can be naturally incorporated in vivo into a RNA molecule, such as a messenger RNA, by the host.

Thus, a "naturally-occurring base" is distinct from a synthetic base for which there would be not natural equivalent within said host. However, a "naturally-occurring base" may or may not be a modified base, as both terms shall not be confused in the sense of the invention.

An uncapped messenger RNA may also be an uncapped and modified messenger RNA, and thus contain at least one modified base.

Thus, an uncapped messenger RNA may also be an uncapped and modified messenger RNA having a (5')ppp(5') guanosine extremity and containing at least one modified base.

An uncapped messenger RNA may also be an uncapped and modified messenger RNA having a (5')ppp(5') guanosine extremity and containing at least one pseudouridine and at least one 5-methylcytosine.

A capped messenger RNA may be a messenger RNA of which the 5'end is linked to a 7-methylguanosine connected to a 5' to 5' triphosphate linkage, and containing naturally-occurring bases or modified bases such as pseudourine or 5-methyl cytosine.

It is also understood that, when both modified and unmodified RNA molecules are used within one embodiment of the invention, they may be used either as mixtures and/or in purified forms.

Tetrafunctional Non-Ionic Amphiphilic Block Copolymer

Tetrafunctional non-ionic amphiphilic block copolymers have been previously reported in the Art, such as in WO2010026537A1 and/or WO2013128423A1.

Within the invention, the feature "block copolymer" intends to refer to a polymer comprising at least two sets, or blocks, of polymerized monomeric units. A "block" refers to a motif, obtained by polymerization of a monomer, and which may be repeated within the polymer. A block copolymer comprises necessarily at least two distinct kind of blocks of polymerized monomers.

Within the invention, the feature "non-ionic amphiphilic block copolymer" intends to refer to a block copolymer comprising at least one hydrophilic block and at least one hydrophobic block, the blocks being non-ionic, namely they do not contain moiety forming ion.

Within the invention, the feature "tetrafunctional" in relation with "block copolymer" refers to a compound comprising four block copolymers bound to four reactive functions born by a tetrafunctional linking moiety. Otherwise said, a "tetrafunctional block copolymer" comprises four branches of block copolymers bound to a central tetrafunctional linking moiety.

The four block copolymers may be, independently of each other, identical or different, and preferably are identical.

A tetrafunctional non-ionic amphiphilic block copolymer of the invention comprises four branches of block copolymer comprising, each, at least one hydrophilic block and at least one hydrophobic block.

In a tetrafunctional non-ionic amphiphilic block co-polymer useful for the invention the hydrophilic block may be selected in the group consisting of polyoxyalkylenes, polyvinyl alcohols, polyvinyl-pyrrolidones, poly(2-methyl-2-oxazoline), or saccharides, and the hydrophobic block may be selected in the group consisting of polyoxyalkylenes, aliphatic chains, alkylidene polyesters, polyethylene glycol with a benzyl polyether head, and cholesterol.

In particular, the hydrophilic block may be selected in the group consisting of polyoxyalkylenes, polyvinyl alcohols, polyvinyl-pyrrolidones, poly(2-methyl-2-oxazoline), poly-tetrahydrofurane, and the hydrophobic block may be selected in the group consisting of polyoxyalkylenes, aliphatic chains, alkylidene polyesters, polyethylene glycol with a benzyl polyether head, and cholesterol.

More particularly, the hydrophilic block may be selected in the group consisting of polyoxyethylene, polyvinyl alcohols, polyvinyl-pyrrolidones, poly(2-methyl-2-oxazoline), and the hydrophobic block may be selected in the group consisting of polyoxypropylene, aliphatic chains, alkylidene polyesters, polyethylene glycol with a benzyl polyether head, and cholesterol.

According to one embodiment, the hydrophilic blocks of a block copolymer of the invention are comprised of, and preferably consist in, polyethylene oxide units.

According to one embodiment, the hydrophobic blocks of a block copolymer of the invention are comprised of, and preferably consist, in polypropylene oxide units.

According to one embodiment, the hydrophobic blocks of a block copolymer of the invention may be selected in the group consisting of polypropylene oxide units, polycaprolactone units and polylactide units.

According to one embodiment, the hydrophilic blocks of a block copolymer of the invention are comprised of, and preferably consist in, polyethylene oxide units; and the hydrophobic blocks of a block copolymer of the invention are comprised of, and preferably consist, in polycaprolactone units.

According to one embodiment, the hydrophilic blocks of a block copolymer of the invention are comprised of, and preferably consist in, polyethylene oxide units; and the hydrophobic blocks of a block copolymer of the invention are comprised of, and preferably consist in units selected from: polypropylene oxide units, polycaprolactone units and polylactide units.

According to a preferred embodiment, a block copolymer of the invention comprises hydrophilic blocks comprising, and preferably consisting in, polyethylene oxide units, and hydrophobic blocks comprising, and preferably consisting in, polypropylene oxide units.

A tetrafunctional non-ionic amphiphilic block copolymer of the invention comprises at least one terminal hydrophilic or hydrophobic block, which includes at least two, three or four terminal hydrophilic or hydrophobic blocks.

In a preferred embodiment, a tetrafunctional non-ionic amphiphilic block copolymer of the invention comprises at least one terminal hydrophilic block. A "terminal hydrophilic block" is a block located at one end of a copolymer, and in particular at a distal end of a branch of a tetrafunctional polymer of the invention. Preferably, a tetrafunctional non-ionic amphiphilic block copolymer comprises at least two, preferably three, and more preferably four terminal hydrophilic blocks.

According to a preferred embodiment, a block copolymer of the invention comprises at least one, preferably two, even preferably three, and more preferably four terminal oxyethylene unit(s), each at one end of each branch of the polymer.

Preferably, a tetrafunctional non-ionic amphiphilic block copolymer of the invention comprises hydrophilic and hydrophobic blocks in a ratio hydrophilic block/hydrophobic block ranging from about 0.5 to about 1.5.

According to one embodiment, a tetrafunctional non-ionic amphiphilic block copolymer of the invention comprises 40% of polyethylene oxide.

According to one embodiment, a tetrafunctional non-ionic amphiphilic block copolymer of the invention comprises a polyethylene oxide (PEO) to polypropylene oxide (PPO) ratio of 50/56.

According to one embodiment, a tetrafunctional non-ionic amphiphilic block copolymer of the invention comprises a polyethylene oxide (PEO) to polypropylene oxide (PPO) ratio of 61/68.

A tetrafunctional non-ionic amphiphilic tetrafunctional block copolymer useful for the invention may be a (A-B)$_n$L branched block copolymer, with A representing an hydrophilic block, B representing an hydrophobic block, L representing a linking moiety, and n being 4 and figuring the number of (A-B) group linked to L.

According to an alternative embodiment, a tetrafunctional non-ionic amphiphilic tetrafunctional block copolymer useful for the invention may be a (B-A)$_n$L branched block copolymers, with A representing an hydrophilic block, B representing an hydrophobic block, L representing a linking moiety, and n being 4 and figuring the number of (B-A) group linked to L.

According to one embodiment, the hydrophilic block A is a polyoxyethylene block; and the hydrophobic block B is a polyoxypropylene block or a polycaprolactone block or a polylactide block.

Preferably, the hydrophilic block A is a polyoxyethylene block, and the hydrophobic block B is a polyoxypropylene block.

The tetravalent linking moiety L may be selected from:

an alkylene diamino moiety, in particular a $C_1$-$C_6$ or even $C_2$-$C_6$ alkylene diamino moiety; and preferably is an ethylene diamino moiety; or an alkylene or a cycloalkylene of 5 to 8 carbons or a phenylene; in particular a cycloalkylene of 5 or 6 carbons, or a radical of formula (Y):

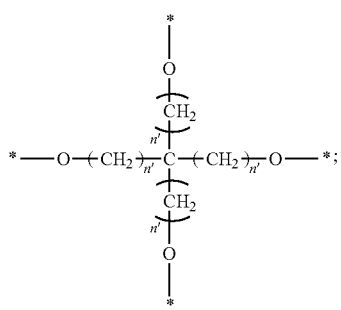

wherein n' is equal to 1, 2, 3, 4, 5 or 6, and most preferably is equal to 1.

According to specific embodiments, a tetrafunctional non-ionic amphiphilic block copolymer useful for the invention may be of formula (Ia), (Ib) or (Ic):

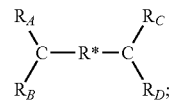

(Ia)

or

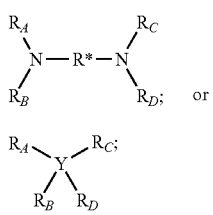

(Ib)

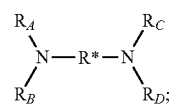

(Ic)

or wherein $R_A$, $R_B$, $R_C$, $R_D$ represent independently of one another:

*-[B]$_i$-[A]$_j$-Re or
*-[A]$_i$-[B]$_j$-Re;

in which

A is a hydrophilic block, preferably comprising or consisting of polyethylene oxide units, B is a hydrophobic block as defined above, Re means an hydrogen atom, a glycosyl residue, a methyl or methoxy group, a $C_2$-$C_6$ alkyl or alkoxy group, an acid, a dicarboxylic acid such as an ethanedioic or propanedioic or butanedioic acid, an amine, an aminoglycoside, or an amide, i has values from about 3 to about 125, which includes equal or less than 60, j has values from 3 to about 85, which includes equal or less than 50, and Y is as defined above, R* is an alkylene of 1 to 6 carbons, a cycloalkylene of 5 to 8 carbons or a phenylene, in particular an alkylene diamine moiety and preferably is an ethylene diamine moiety.

According to a particular embodiment, a tetrafunctional non-ionic amphiphilic block copolymer useful for the invention may thus be of formula (Ia) or (Ib):

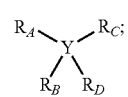

(Ia)

(Ib)

wherein $R_A$, $R_B$, $R_C$, $R_D$, R* and Y are as defined above.

Preferably, $R_A$, $R_B$, $R_C$, $R_D$ represent independently of one another

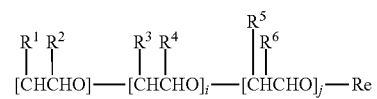

in which

Re means an hydrogen atom, a glycosyl residue, a methyl, an acid, an amine, an aminoglycoside, or an amide, i has values from about 3 to about 125, in particular from about 10 to about 100, and more particularly from about 10 to about 60, and j has values from 3 to about 85, in particular from about 10 to about 50, in particular from about 10 to about 20, and more particularly equal to or greater than 13, for $R^1$ and $R^2$, either (a) both are hydrogen or (b) one is hydrogen and the other is methyl, for $R^3$ and $R^4$ either (a) both are hydrogen or (b) one is hydrogen and the other is methyl, and if both of $R^3$ and $R^4$ are hydrogen, then one $R^5$ and $R^6$ is hydrogen and the other is methyl, or if one of $R^3$ and $R^4$ is methyl, then both of $R^5$ and $R^6$ are hydrogen.

Most preferably, $R_A$, $R_B$, $R_C$, $R_D$ as defined above are identical.

Preferably, a tetrafunctional non-ionic amphiphilic block copolymer is of formula (Ia) wherein:

i has values from about 3 to about 125, in particular from about 10 to about 100, and more particularly from about 10 to about 60, and j has values from 3 to about 85, in particular from about 10 to about 50, in particular from about 10 to about 20, and more particularly equal to or greater than 13.

Preferably, R* is an alkylene of 2, 4 or 6 carbons, a cycloalkylene of 5 to 8 carbons or a phenylene; and most preferably is an alkylene of 2, 4 or 6 carbons.

Protocols for the synthesis of those polymers have already been described in the Art, such as in WO2010026537A1 and/or WO2013128423A1 (See also: Schmola, I. R.; *J. Am. Oil Chem.*; Soc. 54:110; 1977 & Schmolka, I. R., *Surf* Sci. Ser. 1967, 1, 300-371). Other block copolymers are available as commercial products. Examples of such block copolymers are commercially available under the references P10321, P10257, P3848, P3152, sold by the company Polymer Source™ (Dorval (Montreal)—Canada).

A tetrafunctional non-ionic amphiphilic block copolymer of the invention, may further comprise at least one terminal block, that is/are optionally glycosylated and/or functionalised.

Thus, and in a non-limitative manner, the at least one terminal block may be glycosylated and/or functionalised by a glycosyl residue, an alkyl chain such as a $C_1$-$C_6$ alkyl, or even a methyl, an acid, a dicarboxylic acid, an amine, an aminoglycoside, or an amide, A tetrafunctional non-ionic amphiphilic block copolymer of the invention, as defined above and herebelow, may comprise at least one terminal block, and preferably one terminal hydrophilic block, that is optionally glycosylated and/or functionalised by a group consisting of aminoglycosides such as tobramycin, paromomycin, kanamycin, neomycin, mannose, glucose, glucosamine.

In particular, a tetrafunctional non-ionic amphiphilic block copolymer of the invention, as defined above, may optionally comprise at least one terminal block, which may include one terminal hydrophilic or hydrophobic block, and preferably one terminal hydrophilic block, conjugated with at least one glycosyl moiety.

In a non-limitative manner, glycosylated tetrafunctional non-ionic amphiphilic block copolymers of the invention and methods for producing said block copolymers are disclosed in WO2013128423A1.

A tetrafunctional non-ionic amphiphilic block copolymer useful for the invention may thus be of formulas (IIa) or (II'a):

$$\text{(IIa)}$$
$$\begin{array}{c} H[OCH_2CH_2]_i-[OCHCH]_j \\ R^1 R^2 \end{array} \begin{array}{c} [CHCHO]_j-[CH_2CH_2O]_iH \\ R^1 R^2 \end{array}$$
$$N-R^*-N$$
$$\begin{array}{c} H[OCH_2CH_2]_i-[OCHCH]_j \\ R^1 R^2 \end{array} \begin{array}{c} [CHCHO]_j-[CH_2CH_2O]_iH \\ R^1 R^2 \end{array}$$

-continued $$\text{(II'a)}$$
$$\begin{array}{c} H[OCHCH]_j-[OCH_2CH_2]_i \\ R^1 R^2 \end{array} \begin{array}{c} [CH_2CH_2O]_i-[CHCHO]_jH \\ R^1 R^2 \end{array}$$
$$N-R^*-N$$
$$\begin{array}{c} H[OCHCH]_j-[OCH_2CH_2]_i \\ R^1 R^2 \end{array} \begin{array}{c} [CH_2CH_2O]_i-[CHCHO]_jH \\ R^1 R^2 \end{array}$$

in which

R* is an alkylene of 2 to 6 carbons, a cycloalkylene of 5 to 8 carbons or a phenylene, i has values from about 3 to about 125, and j has values from 3 to about 85, wherein for each R', $R^2$ pair, one shall be hydrogen and the other shall be a methyl group, wherein each terminal block is optionally further glycosylated and/or functionalized.

Thus, a tetrafunctional non-ionic amphiphilic block copolymer useful for the invention may thus be of formula (IIa):

$$\begin{array}{c} H[OCH_2CH_2]_i-[OCHCH]_j \\ R^1 R^2 \end{array} \begin{array}{c} [CHCHO]_j-[CH_2CH_2O]_iH \\ R^1 R^2 \end{array}$$
$$N-R^*-N$$
$$\begin{array}{c} H[OCH_2CH_2]_i-[OCHCH]_j \\ R^1 R^2 \end{array} \begin{array}{c} [CHCHO]_j-[CH_2CH_2O]_iH \\ R^1 R^2 \end{array}$$

in which

R* is an alkylene of 2 to 6 carbons, a cycloalkylene of 5 to 8 carbons or a phenylene, and preferably is an alkylene of 2, 4 or 6 carbons, i has values from about 3 to about 125, in particular from about 10 to about 100, and more particularly from about 10 to about 60, and j has values from about 3 to about 85, in particular from about 10 to about 50, in particular from about 10 to about 20, and wherein for each $R^1$, $R^2$ pair, one shall be hydrogen and the other shall be a methyl group.

Alternatively, a tetrafunctional non-ionic amphiphilic block copolymer useful for the invention is of formula (II'a):

$$\begin{array}{c} H[OCHCH]_j-[OCH_2CH_2]_i \\ R^1 R^2 \end{array} \begin{array}{c} [CH_2CH_2O]_i-[CHCHO]_jH \\ R^1 R^2 \end{array}$$
$$N-R^*-N$$
$$\begin{array}{c} H[OCHCH]_j-[OCH_2CH_2]_i \\ R^1 R^2 \end{array} \begin{array}{c} [CH_2CH_2O]_i-[CHCHO]_jH \\ R^1 R^2 \end{array}$$

in which

R* is an alkylene of 2 to 6 carbons, a cycloalkylene of 5 to 8 carbons or a phenylene, and preferably is an alkylene of 2, 4 or 6 carbons, i has values from about 3 to about 125, in particular from about 10 to about 100, and more particularly from about 10 to about 60, and preferably from about 10 to 30 j has values from about 3 to about 85, in particular from about 10 to about 50, more particular from about 10 to about 30, and preferably from about 20 to 25, and wherein for each $R^1$, $R^2$ pair, one shall be hydrogen and the other shall be a methyl group.

In particular, a tetrafunctional non-ionic amphiphilic tetrafunctional block copolymer useful for the invention may be of formula (IIb):

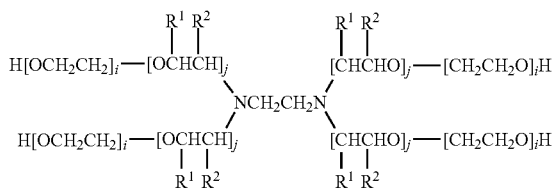

in which i has values from about 3 to about 125, in particular from about 10 to about 100, and more particularly from about 10 to about 60, and j has values from about 3 to about 85, in particular from about 10 to about 50, in particular from about 10 to about 20 or alternatively from about 30 to about 50, and wherein for each $R^1$, $R^2$ pair, one shall be hydrogen and the other shall be a methyl group.

A tetrafunctional non-ionic amphiphilic block copolymer useful for the invention may also be of formula (IIb):

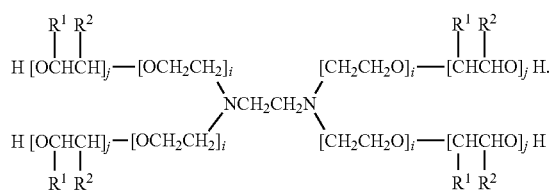

Preferably, i may range from about 3 to about 125, in particular from about 10 to about 100, and more particularly from about 10 to about 60, and j may range from about 5 to about 50, in particular from about 10 to about 25, in particular from about 10 to about 20.

All the tetrafunctional non-ionic amphiphilic block copolymers of the invention for which i and j values are defined, are explicitly considered for each possible combination of i and j.

All the tetrafunctional non-ionic amphiphilic block copolymers of the invention, and their pharmaceutically acceptable salts, are further considered alone or in the form of mixtures, and/or in which at least one terminal block, or even each terminal block, is optionally further glycosylated and/or functionalized.

A block copolymer of the invention may have a molecular weight ranging from 1000 to 35000, which includes from 1000 to 20000 and from 4000 to 35000, in particular ranging from 1000 to 10000 g/mol.

A block copolymer of the invention may comprise, and preferably consist in, an ethylene-oxide units content from about 40% to about 80%, in particular ranging from about 40 to 70%, and more particularly from about 40% to about 60%.

A number of tetrafunctional non-ionic amphiphilic block copolymers of the invention, in particular of non-ionic amphiphilic tetrafunctional block copolymers, are commercially available under generic trade names as "poloxamines".

In particular, non-ionic amphiphilic tetrafunctional block copolymers of the invention are available from BASF (Wyandotte, Mich.) under the tradename Tetronic(™).

Further details of suitable poloxamines for the invention can be found in Surfactant Systems, Eds. Attwood and Florence, Chapman and Hall, London 1983, p 356-361; in The Condensed Encyclopaedia of Surfactants, Ed. Ash and Ash, Edward Arnold, London, 1989, in Non-ionic Surfactants, pp. 300-371, Ed. Nace, Dekker, N.Y., 1996, in Santon, Am. Perfumer Cosmet. 72(4):54-58 (1958); (Dekker, N.Y., 1967), or in U.S. Pat. No. 6,353,055.

Tetrafunctional non-ionic amphiphilic block copolymers which belong to formula (Ib) are also disclosed hereafter.

A tetrafunctional non-ionic amphiphilic block copolymer of the invention may be selected from a group consisting of tetrafunctional non-ionic amphiphilic block copolymers as disclosed here-after, including 304, 414, 616, 618, 704, 904, 1014, 1107 as disclosed here-after and mixtures thereof, more preferably 704 or 904, and most preferably 704.

For reference, a tetrafunctional non-ionic amphiphilic block copolymer 304 (1600 g/mol) of the invention is of sequence:

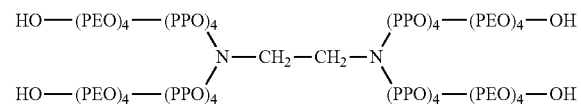

wherein PEO means polyethylene oxide, and PPO means polypropylene oxide.

For reference, a tetrafunctional non-ionic amphiphilic block copolymer 414 (3880 g/mol) of the invention is of formula:

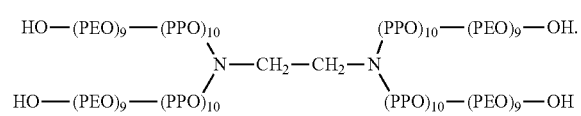

For reference, a tetrafunctional non-ionic amphiphilic block copolymer 616 of the invention is of formula:

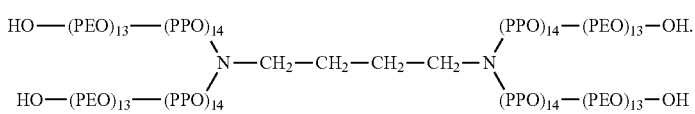

For reference, a tetrafunctional non-ionic amphiphilic block copolymer 618 of the invention is of formula:

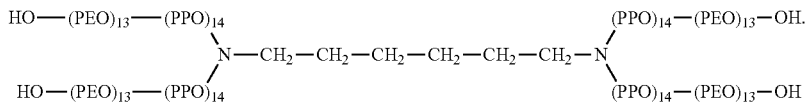

For reference, a tetrafunctional non-ionic amphiphilic block copolymer 704 (5500 g/mol) of the invention is of formula:

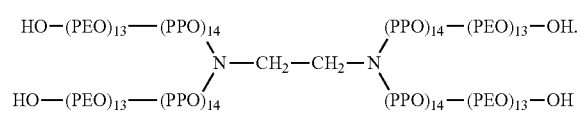

For reference, a tetrafunctional non-ionic amphiphilic block copolymer 904 (6700 g/mol) of the invention is of formula:

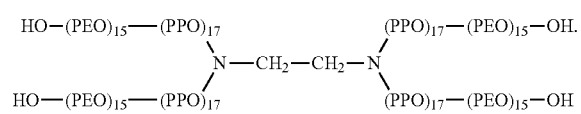

For reference, a tetrafunctional non-ionic amphiphilic block copolymer 1014 (8100 g/mol) of the invention is of formula:

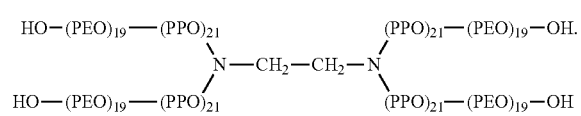

For reference, a tetrafunctional non-ionic amphiphilic block copolymer 606 (5829 g/mol) of the invention is of formula:

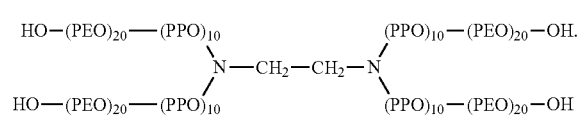

For reference, a tetrafunctional non-ionic amphiphilic block copolymer 608 (5528 g/mol) of the invention is of formula:

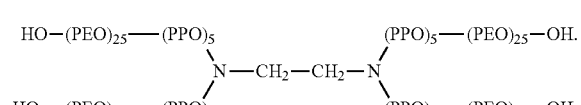

For reference, a tetrafunctional non-ionic amphiphilic block copolymer 1614 (14463 g/mol) of the invention is of formula:

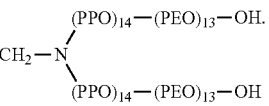

For reference, a tetrafunctional non-ionic amphiphilic block copolymer 7426 (7423 g/mol) of the invention is of formula:

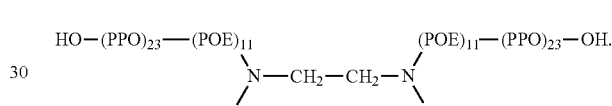

For reference, a functionalized tetrafunctional non-ionic amphiphilic block copolymer 704-NH$_2$ (5568 g/mol) of the invention is of formula:

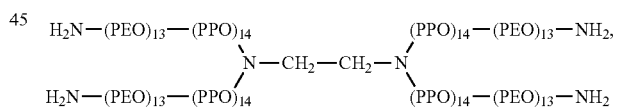

For reference, a functionalized tetrafunctional non-ionic amphiphilic block copolymer 704-Me (5624 g/mol) of the invention is of formula:

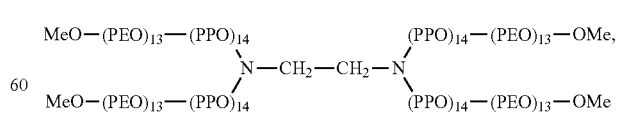

wherein Me is (—CH$_3$).

For reference, a functionalized tetrafunctional non-ionic amphiphilic block copolymer 704-Oox (5808 g/mol) of the invention is of formula:

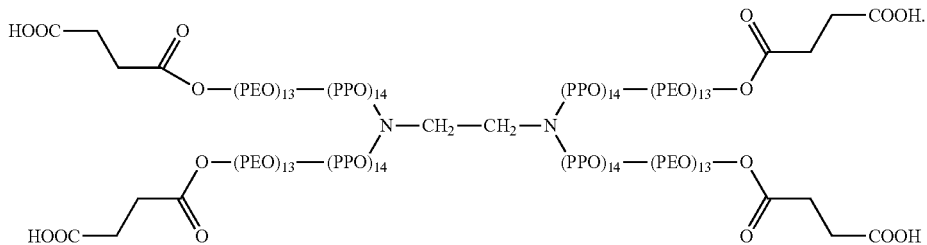

For reference, a functionalized tetrafunctional non-ionic amphiphilic block copolymer 704-Nox (5900 g/mol) of the invention is of formula:

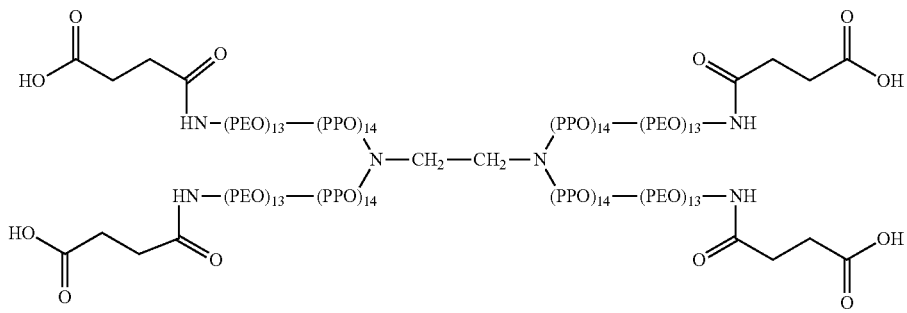

For reference, a tetrafunctional non-ionic amphiphilic block copolymer 704-paromomycine (7700 g/mol) of the invention is of formula:

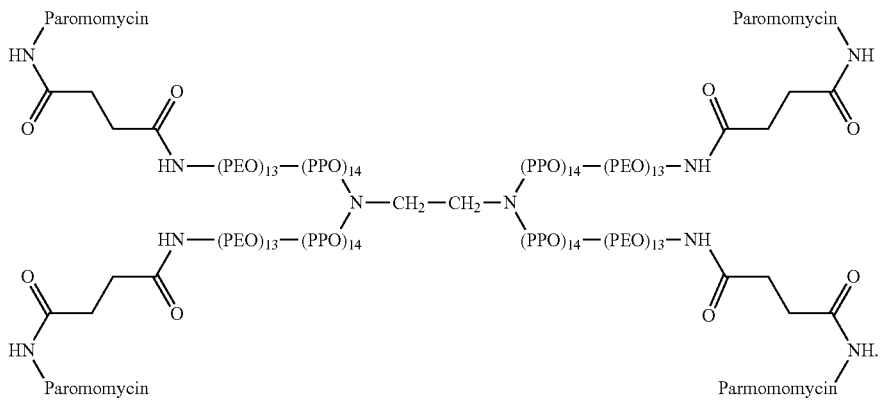

Tetrafunctional non-ionic amphiphilic block copolymers which belong to formula (Ib) are also disclosed hereafter.

For reference, a tetrafunctional PLA-POE non-ionic amphiphilic block copolymer "3648" (8996 g/mol) of the invention is of formula:

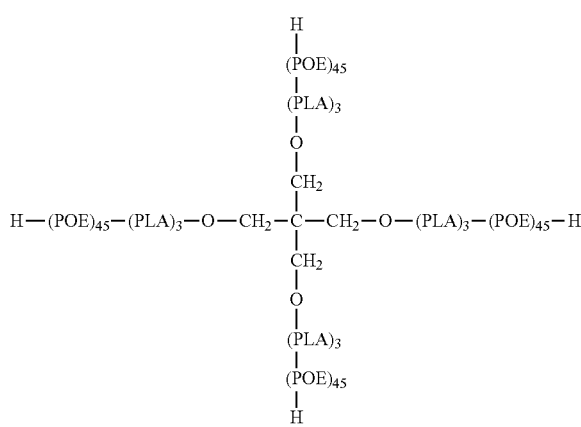

wherein POE means polyethylene oxide and PLA means polylactide.

For reference, a tetrafunctional POE-PCL non-ionic amphiphilic block copolymer "10321" (4332 g/mol) of the invention is of formula:

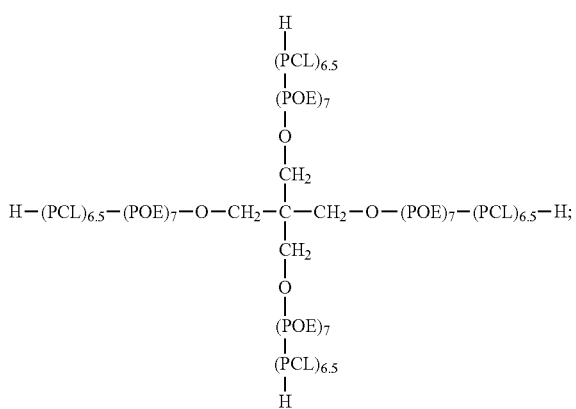

wherein POE means polyethylene oxide and PCL means polycaprolactone. Of note, the value "6.5" refers to block copolymers of which the value is either 6 or 7, and mixtures thereof.

For reference, a tetrafunctional POE-PPO non-ionic amphiphilic block copolymer "10257" (7332 g/mol) of the invention is of formula:

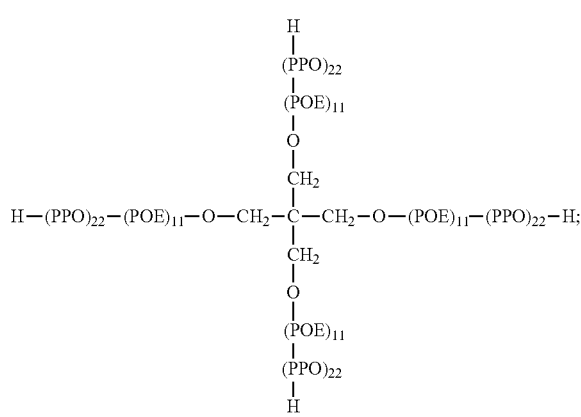

wherein POE means polyethylene oxide and PPO means polypropylene oxide.

According to exemplary embodiments, the tetrafunctional non-ionic amphiphilic block copolymer is selected from:

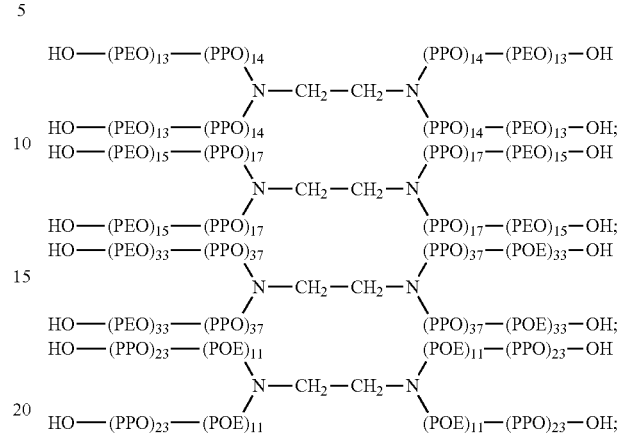

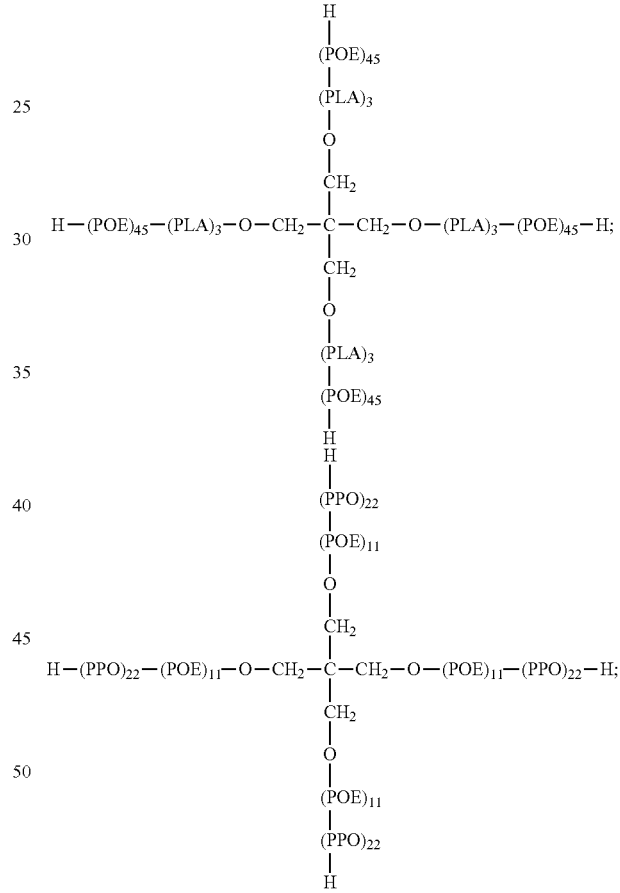

wherein each terminal block is optionally further glycosylated and/or functionalized; or one of its pharmaceutically acceptable salts; and mixtures thereof.

As stated previously, the block copolymers of the invention are unexpectedly used in very low concentrations for efficiently transfecting RNA compared to the usual concentration considered for transfecting DNA. Indeed here it has be observed that optimal concentration of block copolymers is 75 fold lower to that used for optimal in vivo delivery of DNA.

In particular, and as shown from the examples; RNA molecules such as mRNAs, may be transfected at a concentration equal or lower than $20.10^{-4}$% (w/v), or even equal or lower than $10.10^{-4}$% (w/v), and/or as low as $5.10^{-4}$% (w/v).

In the sense of the invention, percentages related to concentrations of RNA molecules are expressed in (w/v), and as described above.

Pharmaceutical Compositions and Methods of Treatment

The invention relates to tetrafunctional non-ionic amphiphilic block copolymers as such and as defined above, and their pharmaceutically acceptable salts, and mixtures thereof.

The invention further relates to compositions, and more particularly to a pharmaceutical composition, comprising at least an effective amount of at least one tetrafunctional non-ionic amphiphilic block copolymer as defined above.

Thus, the invention also relates to a composition, and more particularly to a pharmaceutical composition, comprising at least an effective amount of at least one tetrafunctional non-ionic amphiphilic block copolymer as a vehicle for at least one RNA molecule, such as a capped or uncapped mRNA.

Thus, the invention relates to a pharmaceutical composition comprising a tetrafunctional non-ionic amphiphilic block copolymer, as a vehicle for at least one RNA molecule, such as a capped or uncapped mRNA, and preferably at least one uncapped mRNA.

Thus the invention also relates to any of the tetrafunctional non-ionic amphiphilic block copolymers as described above, for the preparation of a medicament and/or a pharmaceutical composition, including compositions for use for intracellular delivery and gene therapy.

A pharmaceutical composition of the invention may comprise a vehicle that is pharmaceutically acceptable, and suitable for any mode of administration, which includes enteral and parenteral administration, which includes topical administration, needle injection and needle-free injection.

In the sense of the invention, a needle-free injection may include jet injection. Jet injection is known in the Art, as shown for instance in WO2015024667A1.

Jet injection includes forcing the passage of a pharmaceutical composition as described above, optionally containing further suitable excipients, through an orifice and thereby generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the nucleic acid according to the invention.

A pharmaceutical composition of the invention may comprise a vehicle that is pharmaceutically acceptable, in particular for an injectable formulation, in particular for systemic injection, injection directly into the desired organ or for topical administration, for example to the skin and/or mucous membranes. They may be sterile isotonic solutions or dry, in particular lyophilized, compositions which, by means of the addition, according to the case, of sterilized water or of physiological saline, make it possible to constitute injectable solutes.

It is clear that the doses used for the injection and also the number of administrations may be adjusted by means of various parameters, and in particular as a function of the method of administration under consideration, of the pathology involved, of the nature of the negatively charged macromolecules to be administered, of the therapeutic or prophylactic effect to be reached, of the individual to be treated, and of the conditions to be treated or prevented.

For example, in the field of gene therapy, the doses will depend of the gene to be expressed or repressed, or of the nature of the messenger RNA.

Within the meaning of the invention, the term "to prevent" with respect to a disease is to be understood as meaning to reduce the risk of occurrence of said disease.

With regards more particularly to the method of administration, it may involve either direct injection into the tissues or the circulatory system, or treatment of cells in culture followed by re-implantation in vivo by injection or graft.

For the purpose of the present invention, the team "internal administration" means that a composition of the invention is compatible with administration into the tissue of an organism, for example a muscle (intra-muscular), intradermally or subcutaneously. Furthermore, topical, oral, pulmonary, nasal and mucosal, such as, for example, buccal, vaginal or rectal, administration may be used.

The compositions according to the invention are particularly advantageous from a therapeutic point of view, in particular in gene therapy, and for use as a medicament.

The compositions thus prepared are then injected into cells, preferably muscle cells or dendritic cells.

Insofar as a composition of the invention is particularly advantageous for increasing the amount of proteins synthesized by the transfected cells.

The administration can be carried out topically, directly into the cells under consideration, or by means of one of the routes of administration discussed above.

According to one preferred embodiment, a block copolymer of the invention is formulated in a Tyrode's medium ($CaCl_2$ 3 mM, $MgCl_2$ 2 mM, KCl 6 mM, NaCl 140 mM, glucose 10 mM, and Hepes 10 mM, pH 7.4; Tyrode Pharmacology. Philadelphia, 1908, 2nd Edition, 1912) or an equivalent medium.

However other equivalent mediums may also be considered, in particular mediums wherein HEPES is substituted by $NAHCO_3$. Indeed, results have shown (see FIG. 6) that the transfection efficiency is increased with such buffers.

Thus, the invention also relates to a pharmaceutical composition comprising a tetrafunctional non-ionic amphiphilic block copolymer as a vehicle for at least one capped or uncapped mRNA, wherein said tetrafunctional non-ionic amphiphilic block copolymer and mRNA are formulated in a Tyrode's medium or an equivalent medium.

The invention further relates to kits which are suitable for use for intracellular delivery, and/or for gene therapy, comprising:
(i) at least one tetrafunctional non-ionic amphiphilic block copolymer as defined above, and mixtures thereof; and
(ii) at least one RNA molecule, and more particularly at least one capped or uncapped mRNA.

The invention further relates to a method for increasing, improving, and/or maintaining the expression of a protein in an eukaryotic host, comprising a step of transfecting into said host at least one tetrafunctional non-ionic amphiphilic block copolymer, as a vehicle for at least one capped or uncapped mRNA, as defined above.

According to exemplary embodiments, the above-mentioned tetrafunctional non-ionic amphiphilic block copolymer, as vehicles for at least one capped or uncapped mRNA, are particularly efficient for increasing, improving, and/or maintaining the expression of erythropoietin (EPO) in an eukaryotic host.

Thus, the tetrafunctional non-ionic amphiphilic block copolymers of the invention, as vehicles for at least one RNA molecule, especially a capped or uncapped mRNA, are particularly efficient, as a medicament and/or in a pharmaceutical composition, for treating or preventing, and/or reducing the likelihood of occurrence of a disorder associated with impaired erythropoiesis, or impaired red blood cell production, such as disorders selected from anemia and kidney failure.

According to some embodiments, the RNA molecule is a mRNA suitable for the expression of erythropoietin in an individual.

According to some embodiments, tetrafunctional non-ionic amphiphilic block copolymers of the invention, as vehicles for a RNA molecule suitable for the expression of EPO in an individual, are particularly efficient for improving, restoring or stabilizing the percentage of hematocrit in said individual.

A combination as described above is particularly efficient for improving, restoring or stabilizing the percentage of hematocrit in an individual at a physiological level, including above 40%, which includes 40, 41, 42, 43, 44, 45, 46, 47, 48, 49, 50, 51, 52, 52, 54, and 55%.

The present invention will be more fully described with the aid of the following examples and figures which should be considered as illustrative and nonlimiting.

FIGURES

Figure 1B:
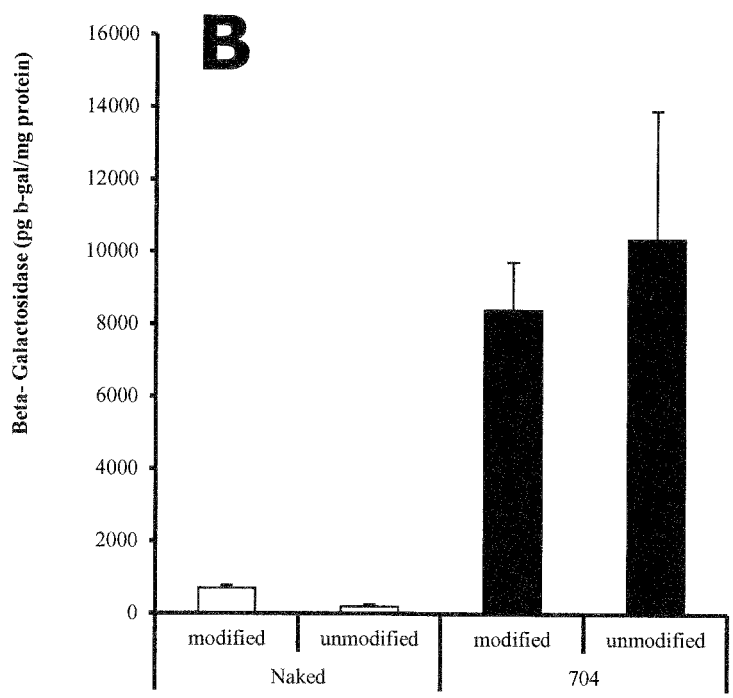
Figures 1C, 1D:
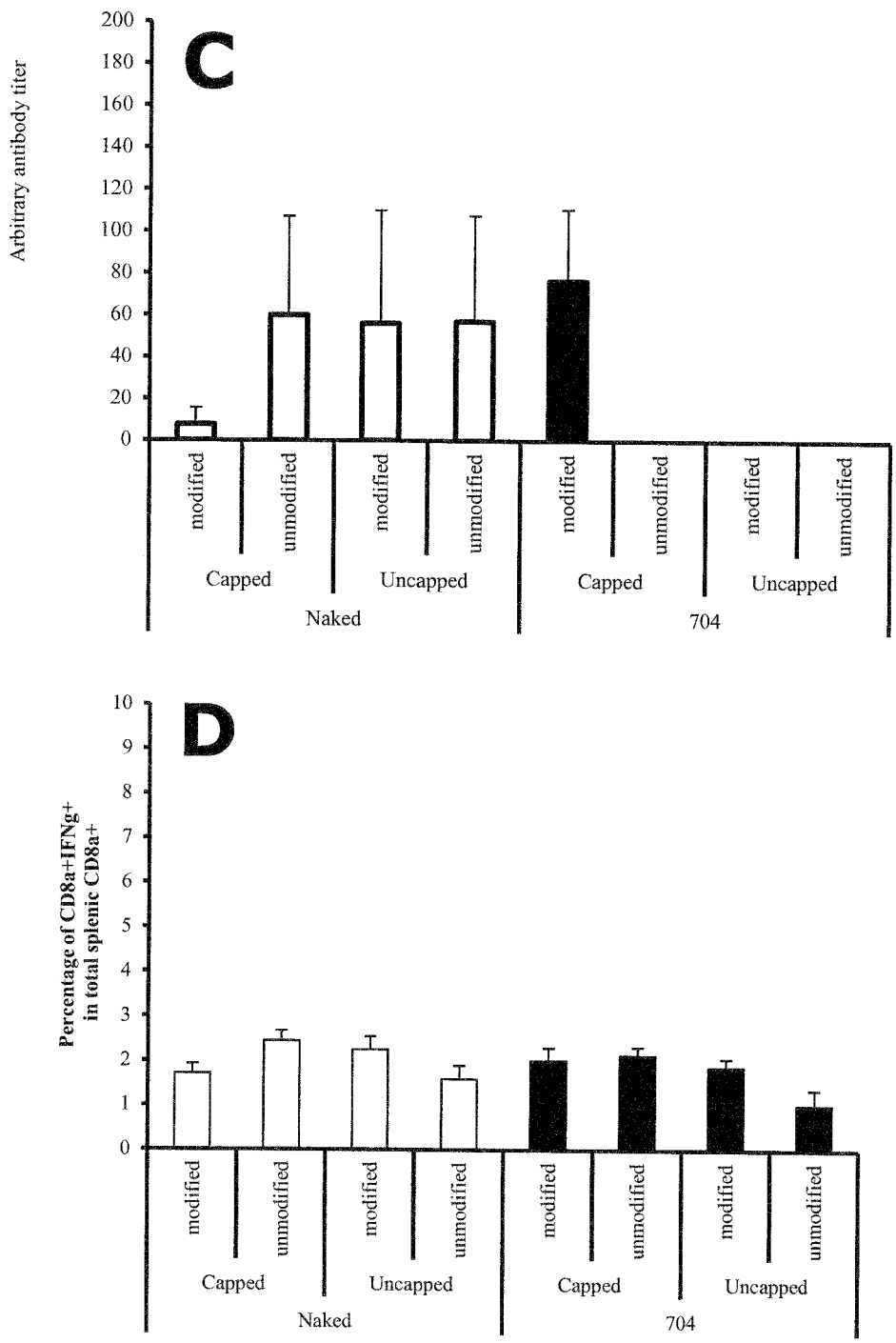

FIG. 1. Infuence of the mRNA capping and/or nucleotide modification on β-galactosidase expression in C57B16 mouse skeletal muscle and immune reaction against β-galactosidase. (A) β-galactosidase activity one day after intramuscular injection of 20 μg uncapped fully modified or unmodified mRNA either naked or formulated with $20.10^{-4}$% 704. (B) β-galactosidase activity one day after intramuscular injection of 20 μg capped fully modified or unmodified mRNA either naked or formulated with $20.10^{-4}$% 704. (C) Humoral response at 42 days after a vaccination scheme consisting in one intramuscular injections at day 0 and 21 of 20 μg capped or uncapped modified and/or unmodified mRNA either naked or formulate with $20.10^{-4}$% 704. Each column represents the mean antibody titer determined by ELISA of at least eight individual mice. (D) Specific CD8+IFNγ+ β-galactosidase cells percentage. Splenocytes were prepared at day 42 stimulated overnight with murine dendritic cell line (Jaws) transfected with ICAFectin®441 and plasmid DNA encoding β-galactosidase or as control with plasmid DNA encoding the AlphaFetoproteine. After washing, cells were stained with an anti-CD8 antibody and anti-IFN-γ. Each column represents the percentage of CD8+IFNγ cells in total splenic CD8+ +/− SEM of at least six individual mice.

Figure 2:
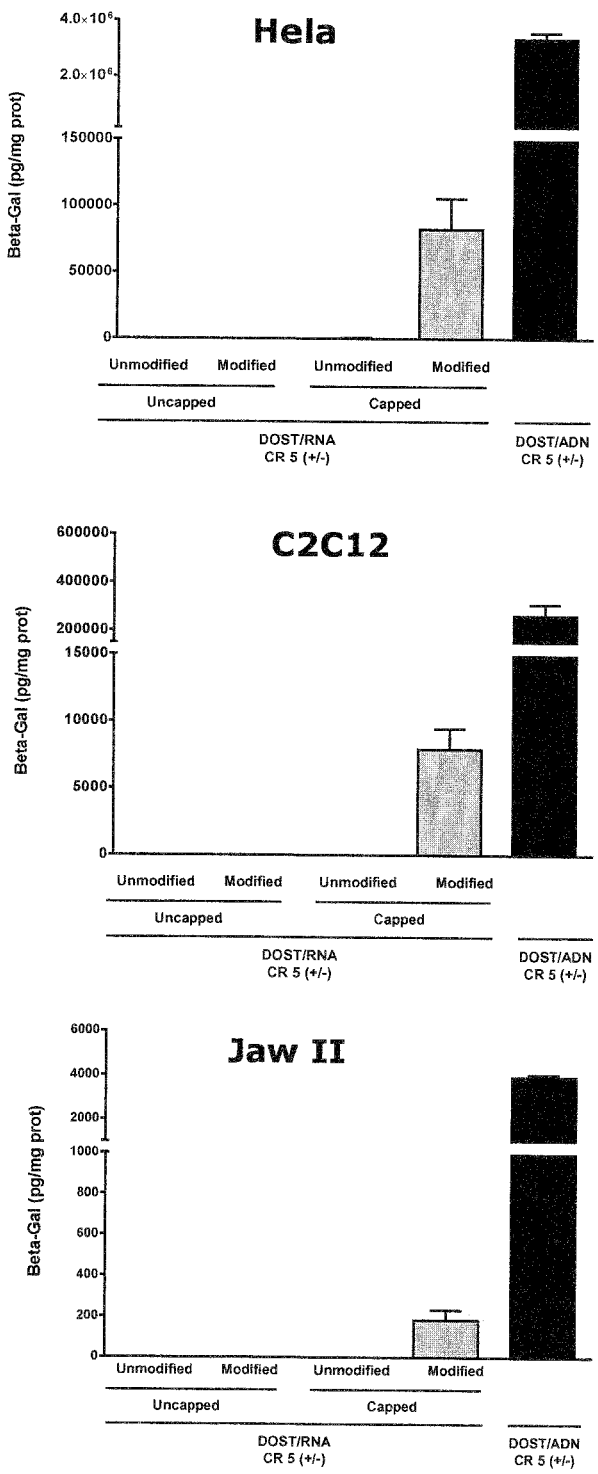

FIG. 2. Infuence of the mRNA capping and/or nucleotide modification on β-galactosidase expression in cells in culture. Hela (upper part of FIG. 2), C2C12 (middle of FIG. 2) and JAWII cells (bottom of FIG. 2) were transfected with aminoglycoside lipidic derivative DOST at a charge ratio of 5 (+/−) with 0.5 μg of formulated mRNA or formulated DNA encoding beta galactosidase. RNA molecules were either capped or uncapped with fully modified U and C by Pseudo-U or 5-Methyl-Cytosine or unmodified U and C. After 24 h, cells were collected and beta galactosidase expression was measured. Results are expressed by pg of beta galactosidase per mg of cellular protein (pg/mg prot). Data are shown as the average ±SEM of the (beta gal (pg/mg prot) of the transfected cells. As control, cells transfected with RNA alone or DNA alone gave no significant expression of the beta galactosidase.

FIG. 3. Mouse hematocrit as a function of time after injection of block copolymer formulations. (A) Mouse hematocrit as a function of time after intramuscular injection of 704/RNA formulations containing 20 μg mRNA encoding murine EPO and $10\times10^{-4}$% (open circles), $20\times10^{-4}$% (open squares) or $100\times10^{-4}$% (open triangles) 704. As control, mice were also injected with 20 μg of naked RNA encoding murine EPO (solid circles). As control a group of mice was also uninjected (solid squares). (B) mouse haematocrit as a function of time after intramuscular injected of 704/DNA formulation containing 10 μg of plasmid. DNA encoding murine EPO and 0.15% 704 (open circles). As control, mice were also injected with 10 μg of naked DNA encoding murine EPO (close circles). As control a group of mice was also uninjected (solid squares). (C) mouse haematocrit as a function of time after intramuscular injection of 904/RNA formulations containing 20 μg mRNA encoding murine EPO and $10\times10^{-4}$% 4 (open circles), $20\times10^{-4}$% (open squares) or $100\times10^{-4}$% (open triangles) 904. As control, mice were also injected with 20 μg of naked RNA encoding murine EPO (solid circles). As control a group of mice was also uninjected (solid squares).

FIG. 4: Modulation of the hematocrit in mice intramuscularly injected with block copolymer/RNA formulations and 704/DNA formulations (B). (A) Six mice were treated 2 times at day 0 and 42 with 2 successive injections with one week interval. Treatments consisted of 20 μg mRNA encoding murine EPO either naked (open triangles) or formulated with and $100\times10^{-4}$% (solid squares) 904 and $20\times10^{-4}$% (solid circles) 704. At day 100 after the beginning of the treatment mice received a single injection consisting of 20 μg mRNA encoding EPO either naked (open triangles) or formulated with $100\times10^{-4}$% (solid squares) 904 and $20\times10^{-4}$% (w/v) (solid circles) 704. At day 134 after the beginning of the treatment, mice received a single injection of 20 μg mRNA encoding the murine EPO with $100\times10^{-4}$% 904 (solid squares). As control, mice were also uninjected (open squares). Dotted lines represent the fluctuation over the of the hematocrit of healthy non injected mice. (B) Six mice were treated at day 0, 56 and 100 with 10 μg naked DNA (open diamond) or formulated with 0,15% 704 (solid diamond). As control, mice were also uninjected (open squares). Dotted lines represent the fluctuation over the of the hematocrit of healthy non injected mice. (C) Murine EPO expression measured at day 135 in serum of mice 24 hours after injection of 20 μg RNA encoding murine EPO either naked of formulated with $100\times10^{-4}$% 904 and 10 μg plasmid DNA encoding EPO either naked or formulated with 0.15% 704. Each bar represents the mean+/− SEM of 6 individual values. (D) Humoral response at 170 days after the beginning of the treatment with either DNA or mRNA encoding the murine EPO formulated with tetra functional block copolymers. Each column represents the mean antibody amount against murine EPO measured in the serum of mice injected with the various compositions, determined by ELISA using a standard curve made of known amount of commercially available antibodies against murine EPO.

Figure 5:
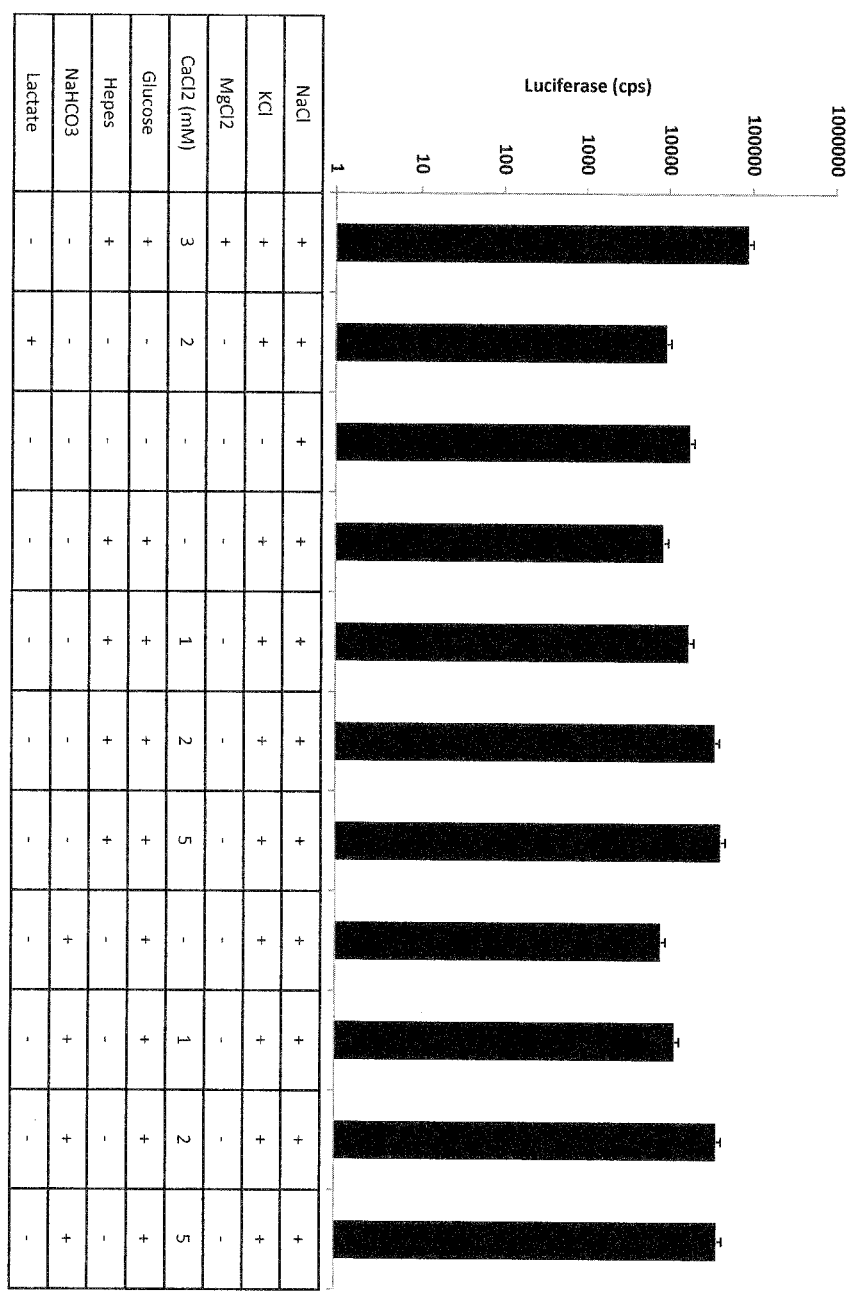

FIG. 5: Luciferase expression in mouse skeletal muscle after intramuscular injection of mRNA formulated with 704 at $20.10^{-4}$%. Luciferase activity 24 hours after intramuscular injection of 10 μg mRNA formulated with 704 in various medium buffered either with Hepes, NaHCO3 or sodium Lactate corresponding respectively to pH of 7.4, 7.4 and 6.7. The effect of the concentration of CaCl2 ranging from 1 to 5 mM on luciferase expression was also measured on two different medium buffered either by Hepes or NaHCO3. As a control a group of mice was injected with a medium consisting of 150 mM NaCl. Each column represents the mean+/− SEM of at least six individual values.

Figure 6:
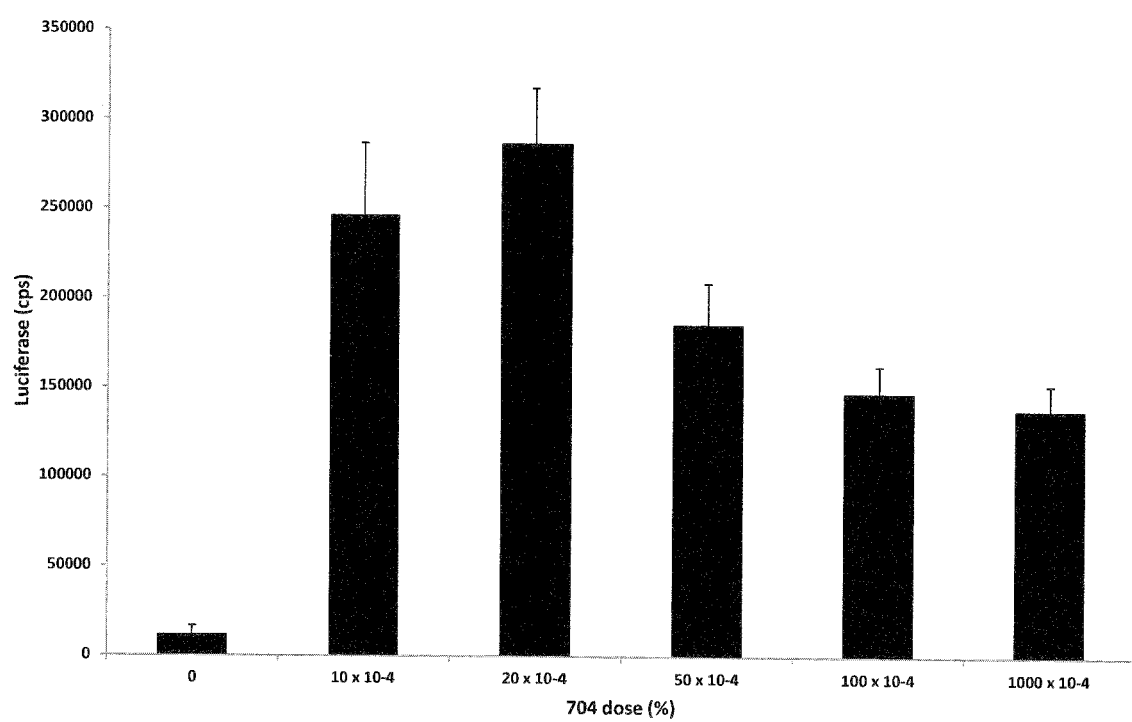

FIG. 6: Luciferase expression in mouse skeletal muscle after intramuscular injection of mRNA formulated with 704 at various concentrations. Luciferase activity 24 hours after intramuscular injection of 10 μg mRNA formulated with 704 at various concentrations ranging from $10.10^{-4}$ to $1000.10^{-4}$% (w/v). Each column represents the mean+/− SEM of at least six individual values.

Figure 7:
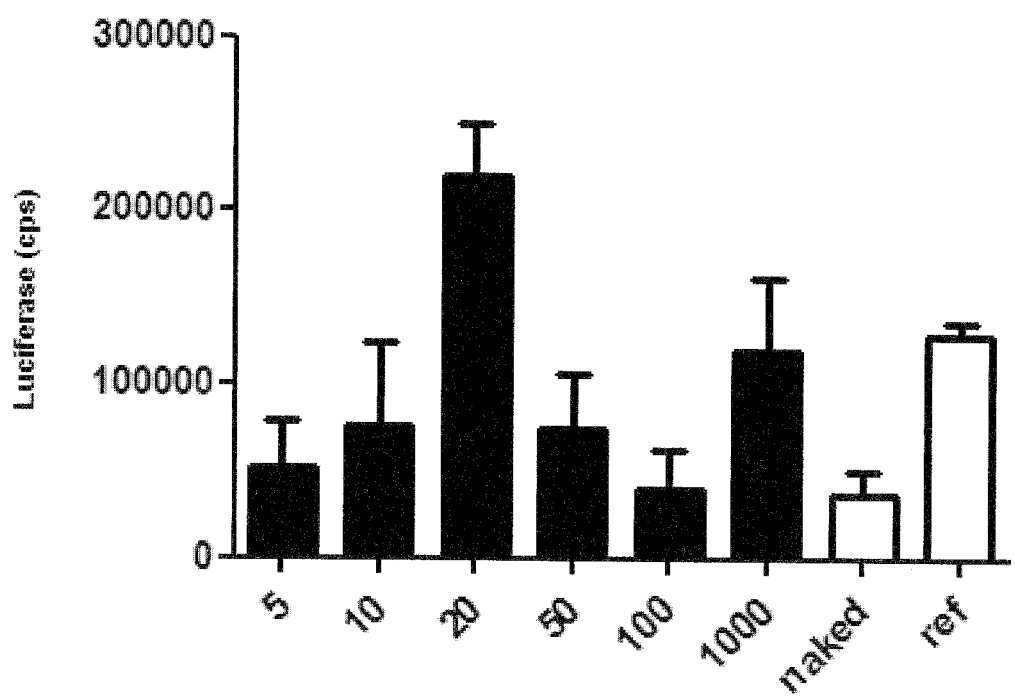

FIG. 7: Luciferase expression in mouse skeletal muscle after intramuscular injection of capped modified mRNA either naked or formulated with tetrafunctional PEO-PPO amphilic block copolymer of 14 463 g/mol. Luciferase activity 24 hours after intramuscular injection of 5 μg mRNA formulated with the block copolymer at various concentrations ranging from 5 to $1000.10^{-4}$% (w/v). Each column represents the mean+/− SEM of at least six individual values. The column "naked" relates to the expression of luciferase after administration of the same mRNA but without the block copolymer. The column "ref" relates to the expression of luciferase after administration of the same rnRNA in combination with the tetrafunctional block copolymer 704. when administered at a concentration of about $20.10^{-4}$% (w/v).

Figure 8:
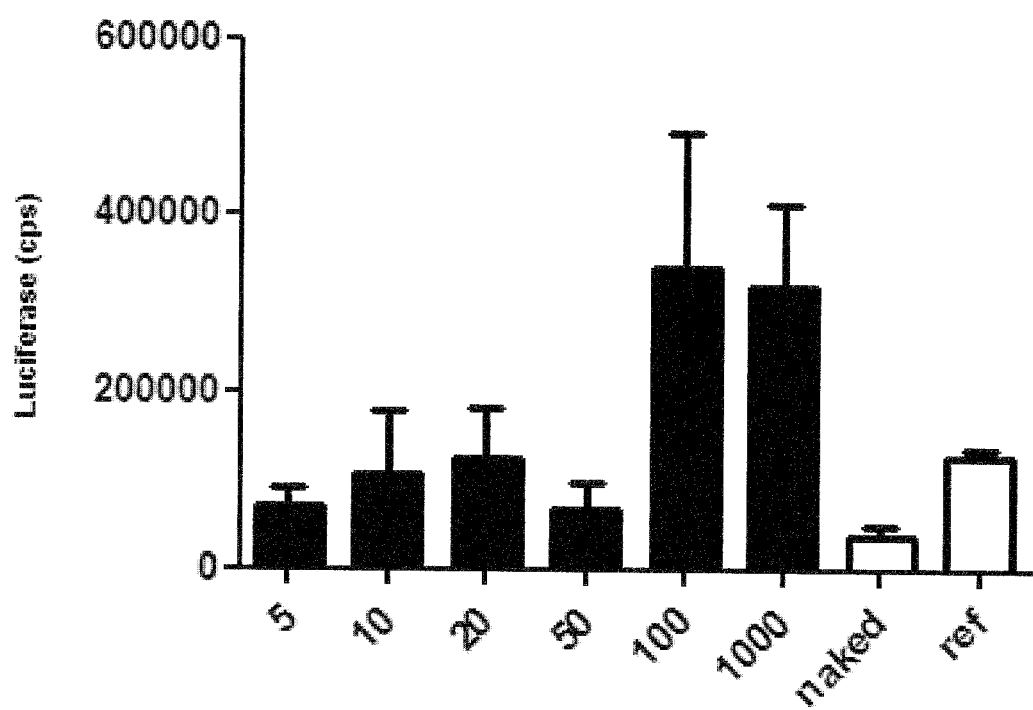

FIG. 8: Luciferase expression in mouse skeletal muscle after intramuscular injection of capped modified mRNA either naked or formulated with tetrafunctional PPO-POE amphilic block copolymer of 7423 g/mol. Luciferase activity 24 hours after intramuscular injection of 5 μg mRNA formulated with the block copolymer at various concentrations ranging from 5 to $1000.10^{-4}$% (w/v). Each column represents the mean+/− SEM of at least six individual values. The column "naked" relates to the expression of luciferase after administration of the same mRNA but without the block copolymer. The column "ref" relates to the expression of luciferase after administration of the same rnRNA in combination with the tetrafunctional block copolymer 704. when administered at a concentration of about $20.10^{-4}$% (w/v).

Figure 9:
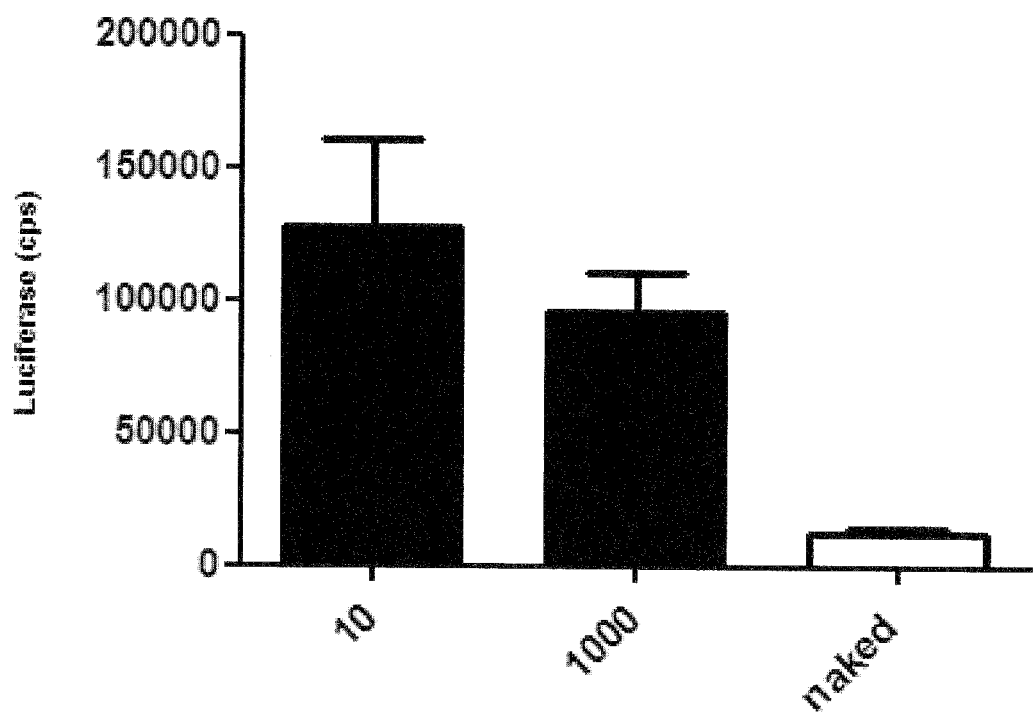

FIG. 9: Luciferase expression in mouse skeletal muscle after intramuscular injection of capped modified mRNA either naked or formulated with tetrafunctional PLA-POE amphilic block copolymer of 8996 g/mol. Luciferase activity 24 hours after intramuscular injection of 5 μg mRNA formulated with the block copolymer at 10 and $100.10^{-4}$% (w/v). Each column represents the mean+/− SEM of at least six individual values. The column "naked" relates to the expression of luciferase after administration of the same mRNA but without the block copolymer.

Figure 10:
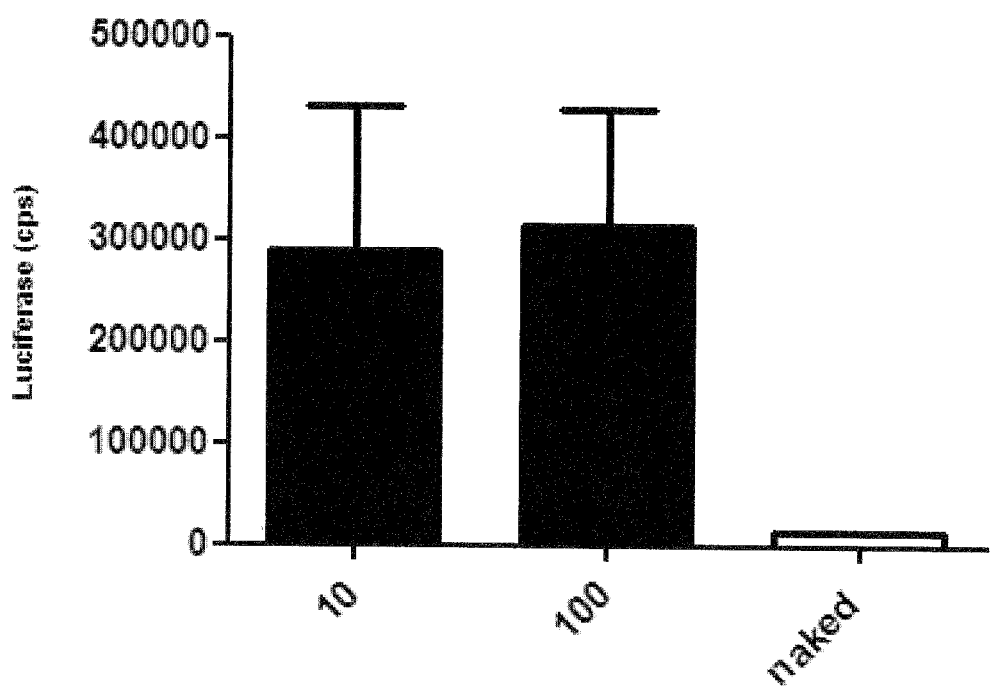

FIG. 10: Luciferase expression in mouse skeletal muscle after intramuscular injection of capped modified mRNA either naked or formulated with tetrafunctional POE-PPO amphilic block copolymer of 7332 g/mol. Luciferase activity 24 hours after intramuscular injection of 5 μg mRNA formulated with the block copolymer at 10 and $100.10^{-4}$% (w/v). Each column represents the mean+/− SEM of at least six individual values. The column "naked" relates to the expression of luciferase after administration of the same mRNA but without the block copolymer.

FIG. 11: Mouse hematocrit and EPO levels as a function of time after injection of block copolymer formulations. (A) Mouse hematocrit as a function of time after intramuscular injection of 704/RNA formulations containing 20 μg mRNA encoding murine EPO and $10\times10^{-4}$% (open circles), $20\times10^{-4}$% (open squares) or $100\times10^{-4}$% (open triangles) 704. As control, mice were also injected with 20 μg of naked RNA encoding murine EPO (solid circles). As control a group of mice was also uninjected (solid squares). (B) mouse haematocrit as a function of time after intramuscular injection of 904/RNA formulations containing 20 μg mRNA encoding murine EPO and $10\times10^{-4}$% 4 (open circles), $20\times10^{-4}$% (open squares) or $100\times10^{-4}$% (open triangles) 904. As control, mice were also injected with 20 μg of naked RNA encoding murine EPO (solid circles). As control a group of mice was also uninjected (solid squares). (C) mouse EPO as a function of time after intramuscular injection of 704/RNA formulations containing $20\times10^{-4}$% 704 and various amounts of mRNA encoding murine including 1 (open circles), 5 (open diamonds), 10 (open triangles) and 50 μg (open octagon). As control, mice were also injected with 1 (solid circles), 5 (solid diamonds), 10 (solid triangles) and 50 μg (solid octagon) of naked RNA encoding murine EPO. As control a group of mice was also uninjected (solid squares, dotted line). (D) Hematocrit level as a function of time of the same described in (C). After 10 hours, mouse EPO levels were measured in serum (E) and in the muscles (F) of mice injected intramuscularly either with plasmid DNA encoding murine EPO formulated with 704 (solid symbols) or with mRNA formulated with 704 (empty symbols). Each symbol represents the mean+/− SEM of at least 6 individual mice.

Figure 12:
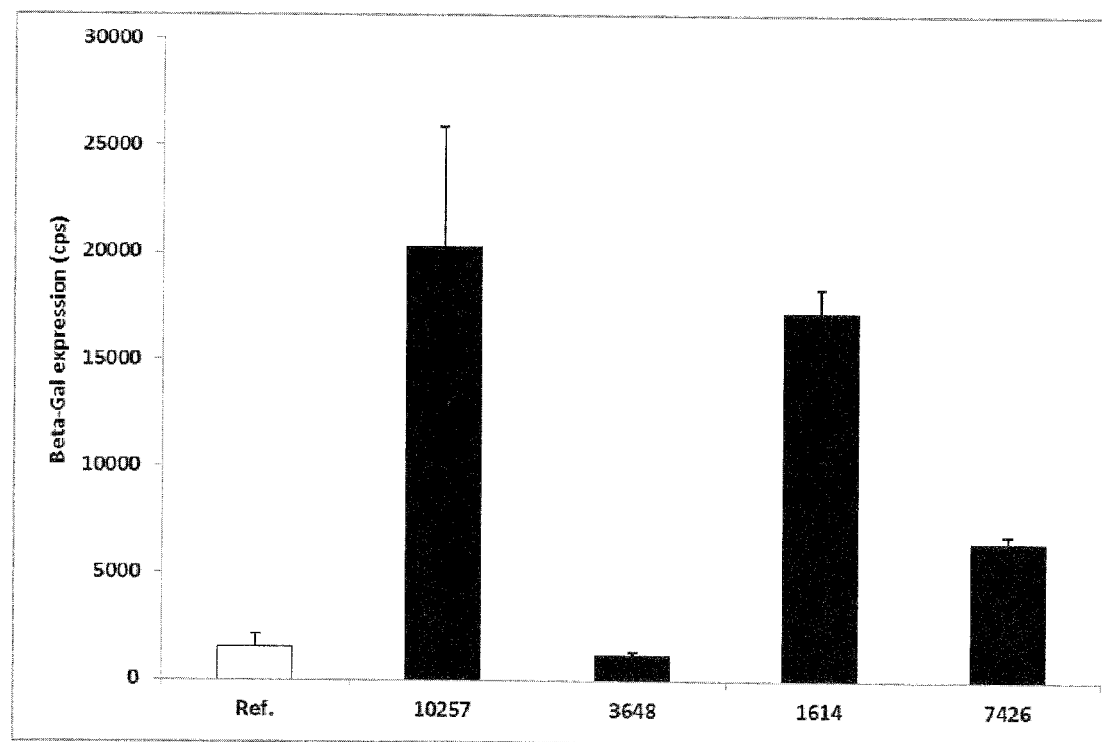

FIG. 12: β-galactosidase expression after intramuscular injection of uncapped modified mRNA in combination with block copolymers of the invention. The y-axis represents the β-galactosidase expression in cps. The x-axis represents from left to right, the datasets corresponding to block copolymers 704; 10257; 3648; 1614 and 7426.

Figure 13:
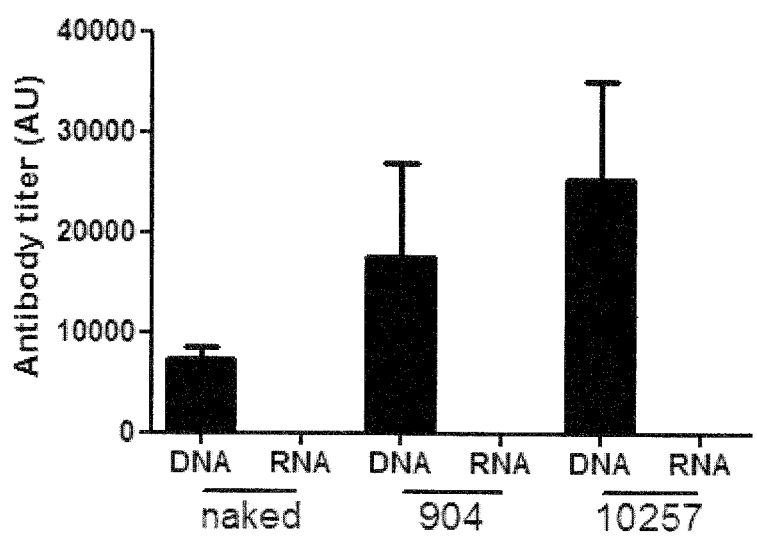

FIG. 13: Humoral response in mice at day 35 after 2 intramuscular injections of capped unmodified mRNA at day 0 and 21, in the presence of block copolymers 904 and 10257. The y-axis represents the mean antibody titer determined ELISA of at least six individual mice. The x-axis represents from left to right the datasets corresponding to naked mRNAs, block copolymers 904 an 10257. For each dataset, the column on the left represents DNA, and the column on the right RNA.

EXAMPLES

Material and Methods
Nucleic Acids Molecules mRNA either capped or not and fully substituted or not for every U or C by Pseudo-U and 5-methyl-C respectively, encoding β-galactosidase, luciferase, Erythropoietin (EPO) were purchased at Trilink (San Diego, USA). The plasmid containing the murine EPO cDNA under the control of the cytomegalovirus (CMV) IE1 promoter/enhancer was constructed by recovering mEPO cDNA by PCR from plasmid pTetO-mEPO (Richard et al., Human Gene Therapy 2005) and introduced into the pcDNA-3 vector (Invitrogen, Cergy Pontoise, France). The pCMV-bGal plasmid (Clontech, St Germain en Laye, France) coding for b-galactosidase controlled by the human cytomegalovirus immediate-early gene promoter was used as antigen. Plasmids were purified from transformed recombinant *Escherichia coli* by means of EndoFree plasmid purification columns (Qiagen, Chatsworth, Calif., USA).

Animals Experiments and Nucleic Acids Formulations

All animal experiments were performed in accordance with the guidelines of the French Institut National de la Santé et de la Recherche Médicale. Eight-week old female Swiss and C57bl/6 mice were obtained from Janvier (Le Genest Saint Isle, France). At least six to eight mice were injected in each experimental group. For intramuscular injections, mice were anaesthetized. Fifty microliters of synthetic formulations were injected into shaved tibial anterior muscles at a single site, using a microfine syringe (U100, Becton Dickinson, Rungis, France). Stock solutions of block copolymers were prepared at 2% (w/v) in water and stored at 4° C. Formulations of DNA and mRNA with block copolymer were prepared by equivolumetric mixing of block copolymer in water at the desired concentration with plasmid DNA solution at the desired concentration in buffer.

Cell Culture

Hela, C2C12, JAW II were grown at 37° C., 5% CO2 in Dublecco's modified Eagles medium supplemented with penicillin, streptomycine, L glutamine and 10% fetal calf serum. One day before transfection, cells were plated in 1 mL complete growth medium so that cells reach 70-80% confluence at the time of transfection (0.5–2×10$^5$ cells per well). One day after transfection, cells were harvested and Reporter Lysis Buffer (Promega) supplemented with a protease inhibitor cocktail (Roche Diagnostics) was added to eac wells. After centrifugation at 10,000 rpm for 4 min, luciferase activity was measured from an aliquot of supernatant with Victor$^2$ (PerkinElmer), using a Luciferase Assay System (Promega). Luciferase activity was determined by measuring the light emission after addition of 100 µl of luciferase assay substrate to 10 µl of supernatant.

EPO Expression Analysis

Hematocrit values were measured by microcapillary centrifugation. At different time points after intramuscular injection, mouse blood was collected from the retro-orbital cavity and serum obtained by centrifugation (3 minutes at 1000 g). For plasma samples, blood was collected from the retro-orbital sinus in heparinized tubes and centrifuged 3 minutes at 1000 g. Mouse serum EPO levels were measured by Enzyme Linked-ImmunoAssay (ELISA) following the instructions provided by the manufacturer (R&D Systems).

Anti-Murine EPO Specific Immune Response

Humoral immune responses were measured by ELISA. Briefly, 96-well plates (Nunc Maxisorp) were coated overnight at 4° C. with recombinant murine EPO in 50 mM NaHCO$_3$ pH 9.5, then blocked for 1 hour at room temperature with PBS 0.05% Tween-20 1% bovine serum albumin (BSA) before distributing diluted sera in triplicate. Plates were incubated at 37° C. for 90 minutes, then EPO specific IgG was detected using peroxidase-conjugated goat anti-mouse IgG (Jackson Immunoresearch, Newmarket, UK) diluted 1/5000 in PBS 0.05% Tween-20 1% BSA. Plates were washed three times in PBS 0.05% Tween-20 between steps, and peroxidase activity was revealed with 1 mg/mL OPD in pH5 citrate buffer. Reactions were stopped by addition of 1 M H$_2$SO$_4$, then absorption was measured at 492 nm. Sera were tested at 1/100, 1/1000 and 1/10000, and anti-murine EPO antibody amount was calculated with respect to a standard curve consisting of fixed known amounts of increasing anti-murine EPO commercially available antibodies present in each ELISA plate.

Luciferase Expression

Luciferase protein expression was evaluated by live animal imaging using a PhotonIMAGER Optima system (worldwideweb.biospacelab.com). Briefly, 2 mg of in-vivo luciferase substrate (beetle luciferin substrate, Promega) was injected intraperitoneally in mice and after 10 minutes, mice were anesthetized and luminescent signal will be measured until the baseline was stable. After stabilization of the luminescent signal, measurement of the luminescent was performed for 30 s.

β-Gal Expression

β-Gal expression was quantified in muscle extracts using the BetaGlo Assay System (Promega, Charbonnières, France) according to the manufacturer's protocol.

Anti-β-Gal Specific Immune Response

Humoral immune responses were measured by ELISA. Briefly, 96-well plates (Nunc Maxisorp) were coated overnight at 4° C. with recombinant bGal in 50 mM NaHCO$_3$ pH 9.5, then blocked for 1 hour at room temperature with PBS 0.05% Tween-20 1% bovine serum albumin (BSA) before distributing diluted sera in triplicate. Plates were incubated at 37° C. for 90 minutes, then bGal specific IgG was detected using peroxidase-conjugated goat anti-mouse IgG (Jackson Immunoresearch, Newmarket, UK) diluted 1/5000 in PBS 0.05% Tween-20 1% BSA. Plates were washed three times in PBS 0.05% Tween-20 between steps, and peroxidase activity was revealed with 1 mg/mL OPD in pH5 citrate buffer. Reactions were stopped by addition of 1 M H$_2$SO$_4$, then absorption was measured at 492 nm. Sera were tested at 1/100, 1/1000 and 1/10000, and titres were calculated with respect to doubling dilutions of a control serum present in each ELISA plate.

To measure the percentage of CD8 cell expressing IFNg in the total of splenic CD8 cells, splenocytes were cultured at 5×10$^6$ cells/mL in complete medium. A murine dendritic cell line (JAWS) was transfected with ICAFectin®441 with plasmid DNA encoding either b-galactosidase or murine AlphaFetoprotein, and cells were incubated at 37° C. and 5% CO2. Cells were harvested at 24 hours, then stained with an anti-CD8 antibody and anti-IFNγ and quantified by FACS.

Protocols for the Functionalization of Block Copolymers 704 at their Terminal Blocks I—Preparation of 704-Me 704 (1.07 g, 0.19 mmol, 1 eq.) was dried for 30 min under vacuum, and then dissolved in dry THF (25 mL). At 0° C., NaH (95%, 56 mg, 2.33 mmol, 12 eq.) was added and the mixture was stirred for 30 min at rt. Iodomethane (0.14 mL, 2.33 mmol, 12 eq.) was then added and the mixture stirred at rt overnight. After concentration, the residue was purified by flash chromatography (DCM/MeOH) to give 704-Me (0.93 g, 88%).

II—Preparation of 704-NH$_2$

To a solution of 704 (4.7 g, 0.85 mmol, 1 eq.) in DCM (120 mL) was added p-toluenesulfonyl chloride (1.95 g, 10.25 mmol, 12 eq.). Powdered KOH (0.77 g, 13.67 mmol, 16 eq.) was then added portionwise over 30 min and the mixture was stirred at rt for 2 days. DCM (100 mL) was added and the mixture washed with H$_2$O, brine, dried over MgSO$_4$ and concentrated. The residue was purified by flash chromatography (DCM/MeOH) to give 704-Tos (4.37 g, 84%).

For reference, 704-Tos is of formula:

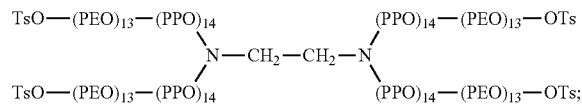

wherein TsO refers to a tosyl group.

To a solution of 704-Tos (4.37 g, 0.71 mmol, 1 eq.) in EtOH (100 mL) was added sodium azide (1.16 g, 17.85 mmol, 25 eq.). The mixture was refluxed for 20 h. After cooling to rt, volatiles were evaporated. The residue was taken up with DCM (100 mL), washed with NaHCO$_3$ $_{sat}$, H₂O, brine, dried over MgSO₄ and concentrated. The residue was purified by flash chromatography (DCM/MeOH) to give 704-N₃ (3.30 g, 82%).

For reference, 704-N₃ is of formula:

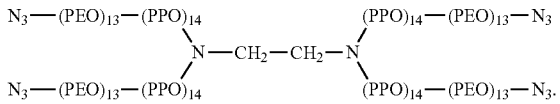

To a solution of 704-N₃ (3.30 g, 0.58 mmol, 1 eq.) in EtOH (60 mL) was added Pd/C (10%, 0.75 g, 0.11 mmol, 0.2 eq.). 3 cycles of vacuum/N₂ were applied, followed by 3 cycles of vacuum/H₂. The mixture was stirred at rt for 2 days, then filtered over a pad of celite, washed with MeOH and concentrated. The residue was purified by flash chromatography (DCM/MeOH) to give 704-NH₂ (2.81 g, 88%).

III—Preparation of 704-NOx

To a solution of 704-NH₂ (0.2 g, 0.036 mmol, 1 eq.) in DCM (20 mL) were successively added Et₃N (0.06 mL, 0.36 mmol, 10 eq.) and succinic anhydride (0.036 g, 0.36 mmol, 10 eq.). The mixture was stirred at rt overnight, then washed with HCl 1 M, H₂O, dried over MgSO₄ and concentrated. The residue was purified by flash chromatography (DCM/MeOH) to give 704-NOx (0.185 g, 87%).

IV—Preparation of 704-Paromo

To a solution of 704-NOx (0.185 g, 0.031 mmol, 1 eq.) in DMF (15 ml) were successively added Paromo(Teoc)-NH₂ (0.224 g, 0.188 mmol, 6 eq.), HBTU (0.083 g, 0.220 mmol, 7 eq.) and DMAP (0.053 g, 0.440 mmol, 14 eq.). The mixture was stirred at 50° C. for 48 h, then concentrated and purified by flash chromatography (DCM/MeOH) to give 704-Paromo(Teoc) (0.149 g, 48%).

For reference, 704-Paromo(Teoc) is of formula:

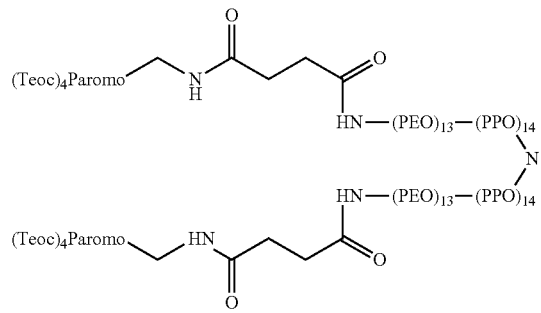 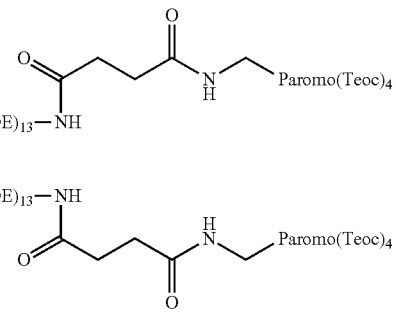

To a solution of 704-Paromo(Teoc) (0.149 g, 0.014 mmol) in DCM (3 mL) was added trifluoroacetic acid (4 mL) at 0° C. After 30 min at 0° C., the mixture was stirred for 1 h at rt, then concentrated. The residue was purified by flash chromatography (DCM/MeOH) to give 704-Paromo (0.042 g, 39%).

V—Preparation of 704-OOx

To a solution of 704 (2 g, 0.36 mmol, 1 eq.) in pyridine (15 mL) was added succinic anhydride (0.36 g, 3.63 mmol, 10 eq.). The mixture was stirred at 55° C. overnight, and then concentrated. The residue was taken up with EtOAc (100 mL), washed with HCl 1 M, H₂O, brine, dried over MgSO₄ and concentrated. The residue was purified by flash chromatography (DCM/MeOH) to give 704-OOx (1.78 g, 84%).

Example 1

In Vivo Transfection of Skeletal Muscles and Immunogenicity, Using Different mRNA Structures and Sequences Purpose: this experiment provides a comparative study of the influence of mRNA capping and nucleotide modification on protein expression on a C57Bl6 skeletal muscle, and also to assess the importance of immune reaction after injection.

As shown from FIG. 1, transfection of a mRNA encoding a β-galactosidase using the tetrafunctional block copolymer 704 as a vehicle allows both (i) efficient protein expression and (ii) minimal immune reaction.

Example 2

In Vitro Transfection of Cultured Cells, Using Different mRNA Structures and Sequences Purpose: this experiment (see FIG. 2) provides evidence that aminoglycoside lipid derivatives are not so satisfactory for mRNA transfection on three different cell lines Example 3

Secretion of Murine Erythropoietin

Purpose: this experiment provides a follow-up, over 20 days, of the injection of an mRNA coding for murine EPO using block copolymer 704 as a vehicle (see FIG. 3).

Example 4

Repeated mRNA and DNA Injection and Mouse Murine EPO Expression

Purpose: this experiment provides a follow-up, over 180 days, of the injection of an mRNA coding for murine EPO using block copolymers 704 or 904 as vehicles, and with repeated mRNA injections. A comparative study is further provided which shows the efficiency of block copolymers 704 and 904 as vehicles for RNA transfection (see FIG. 4).

Example 5

Influence of the Medium of Complexation on Luciferase Expression

Purpose: using Luciferase as a reporter gene, this comparative study provides good evidence that Tyrode's medium and equivalents are endowed with excellent properties regarding RNA transfection using block copolymers of the invention (see FIG. 5).

Example 6

Influence of the Concentration of 704 on Transfection Efficiency

Purpose: This comparative study provides evidence that block copolymers of the invention are very efficient for transfection of RNA molecules even at low concentrations of block copolymers (see FIG. 6).

Example 7

Influence of the Concentration of a Tetrafunctional PEO-PPO Non-ionic Amphiphilic Block Copolymer of 14463 g/mol on Transfection Efficiency Purpose: This comparative study provides evidence of the efficiency of a block copolymer of general formula:

$$\begin{array}{c}\text{HO}-(\text{PEO})_{33}-(\text{PPO})_{37} \quad\quad (\text{PPO})_{37}-(\text{POE})_{33}-\text{OH} \\ \diagdown \quad\quad\quad\quad\quad\quad \diagup \\ \text{N}-\text{CH}_2-\text{CH}_2-\text{N} \\ \diagup \quad\quad\quad\quad\quad\quad \diagdown \\ \text{HO}-(\text{PEO})_{33}-(\text{PPO})_{37} \quad\quad (\text{PPO})_{37}-(\text{POE})_{33}-\text{OH}. \end{array}$$

Indeed, it is observed that block copolymers of the invention are very efficient for transfection of RNA molecules even at low concentrations of block copolymers (see FIG. 7) after intramuscular administration in mouse skeletal muscle. What is more, it has been found that the expression of luciferase after administration of this particular block copolymer is also significantly higher than the expression after administration of the tetrafunctional block copolymer 704.

Example 8

Influence of the Concentration of a Tetrafunctional PEO-PPO Non-ionic Amphiphilic Block Copolymer of 7423 g/mol on Transfection Efficiency Purpose: This comparative study provides evidence of the efficiency of a block copolymer of general formula:

$$\begin{array}{c}\text{HO}-(\text{PPO})_{23}-(\text{POE})_{11} \quad\quad (\text{POE})_{11}-(\text{PPO})_{23}-\text{OH} \\ \diagdown \quad\quad\quad\quad\quad\quad \diagup \\ \text{N}-\text{CH}_2-\text{CH}_2-\text{N} \\ \diagup \quad\quad\quad\quad\quad\quad \diagdown \\ \text{HO}-(\text{PPO})_{23}-(\text{POE})_{11} \quad\quad (\text{POE})_{11}-(\text{PPO})_{23}-\text{OH}. \end{array}$$

Indeed, it is observed that block copolymers of the invention are very efficient for transfection of RNA molecules even at low concentrations of block copolymers (see FIG. 8) after intramuscular administration in mouse skeletal muscle. What is more, it has been found that the expression of luciferase after administration of this particular block copolymer is also significantly higher than the expression after administration of the tetrafunctional block copolymer 704.

Example 9

Influence of the Concentration of a Tetrafunctional PLA-POE Non-ionic Amphiphilic Block Copolymer of 8996 g/mol on Transfection Efficiency Purpose: This comparative study provides evidence of the efficiency of a block copolymer of general formula:

$$\begin{array}{c} \text{H} \\ | \\ (\text{POE})_{45} \\ | \\ (\text{PLA})_3 \\ | \\ \text{O} \\ | \\ \text{CH}_2 \\ | \\ \text{H}-(\text{POE})_{45}-(\text{PLA})_3-\text{O}-\text{CH}_2-\text{C}-\text{CH}_2-\text{O}-(\text{PLA})_3-(\text{POE})_{45}-\text{H} \\ | \\ \text{CH}_2 \\ | \\ \text{O} \\ | \\ (\text{PLA})_3 \\ | \\ (\text{POE})_{45} \\ | \\ \text{H} \end{array}$$

Indeed, it is observed that block copolymers of the invention are very efficient for transfection of RNA molecules even at low concentrations of block copolymers (see FIG. 9) after intramuscular administration in mouse skeletal muscle.

Example 10

Influence of the Concentration of a Tetrafunctional POE-PPO Non-ionic Amphiphilic Block Copolymer of 7332 g/mol on Transfection Efficiency Purpose: This comparative study provides evidence of the efficiency of a block copolymer of general formula:

$$\begin{array}{c} \text{H} \\ | \\ (\text{PPO})_{22} \\ | \\ (\text{POE})_{11} \\ | \\ \text{O} \\ | \\ \text{CH}_2 \\ | \\ \text{H}-(\text{PPO})_{22}-(\text{POE})_{11}-\text{O}-\text{CH}_2-\text{C}-\text{CH}_2-\text{O}-(\text{POE})_{11}-(\text{PPO})_{22}-\text{H} \\ | \\ \text{CH}_2 \\ | \\ \text{O} \\ | \\ (\text{POE})_{11} \\ | \\ (\text{PPO})_{22} \\ | \\ \text{H} \end{array}$$

Indeed, it is observed that block copolymers of the invention are very efficient for transfection of RNA molecules even at low concentrations of block copolymers (see FIG. 10) after intramuscular administration in mouse skeletal muscle.

Example 11

In Vivo Effect of an Entramuscular Administration of Block Copolymers Formulations with an mRNA Encoding EPO, on the Level of Hematocrite in Mice Purpose: This study provides evidence of the variation of EPO and hematocrite in mice over time, after intramuscular administration in mice (see FIG. 11).

Example 12

Influence of Block Copolymers of the Invention as Vehicles for Uncapped Modified mRNAs Purpose: This study provides evidence that block copolymers of the invention are particularly efficient for promoting the expression of uncapped modified mRNAs in an eukaryotic host (see FIG. 12).

β-galactosidase activity one day after intramuscular injection of 15 µg uncapped modified mRNA encoding the β-galactosidase formulated with 704 at $20 \times 10^{-4}$% as reference and 10257 at $100 \times 10^{-4}$%, 3648 at $10 \times 10^{-4}$%, 1614 at $20 \times 10^{-4}$% and 7426 at $100 \times 10^{-4}$%.

The modified RNAs which were used were modified on all Uracile and Cytosine bases, respectively using pseudouridine-5'-triphosphate and 5-methylcytidine-5'-triphosphate nucleotides. Twenty four hours after injection, muscles were harvested and frozen in liquid nitrogen. Beta gal expression was assessed with the help of beta-Glo assay system following manufacturer's instructions (Promega #E4720) in pure muscle extract. The results show that block copolymers 10257, 3648, 1614 and 7426 are particularly efficient as vehicles, even in comparison to the 704 block copolymer.

Example 13

Purpose: This study provides evidence of the lack of immune response after administration of RNA molecules in combination with block copolymers of the invention (see FIG. 13). Mice were injected with 20 µg of plasmid DNA or capped unmodified mRNA encoding beta-galactosidase either naked or formulated with tetrafunctional block copolymer 904 or 10257. Each column represents the mean antibody titer determined by ELISA of at least six individual mice. It is observed that said block copolymers are particularly efficient for intracellular delivery of RNA molecules and for gene therapy.

| SEQUENCE LISTING |
|---|
| SEQ ID NO 1: nucleic acid coding for β-galactosidase E. Coli
ATGTCGTTTACTTTGACCAACAAGAACGTGATTTTCGTTGCCGGTCTGGGAGG
CATTGGTCTGGACACCAGCAAGGAGCTGCTCAAGCGCGATCCCGTCGTTTTAC
AACGTCGTGACTGGGAAAACCCTGGCGTTACCCAACTTAATCGCCTTGCAGCA
CATCCCCCTTTCGCCAGCTGGCGTAATAGCGAAGAGGCCCGCACCGATCGCCC
TTCCCAACAGTTGCGCAGCCTGAATGGCGAATGGCGCTTTGCCTGGTTTCCGG
CACCAGAAGCGGTGCCGGAAAGCTGGCTGGAGTGCGATCTTCCTGAGGCCGA
TACTGTCGTCGTCCCCTCAAACTGGCAGATGCACGGTTACGATGCGCCCATCT
ACACCAACGTAACCTATCCCATTACGGTCAATCCGCCGTTTGTTCCCACGGAG
AATCCGACGGGTTGTTACTCGCTCACATTTAATGTTGATGAAAGCTGGCTACA
GGAAGGCCAGACGCGAATTATTTTTGATGGCGTTAACTCGGCGTTTCATCTGT
GGTGCAACGGGCGCTGGGTCGGTTACGGCCAGGACAGTCGTTTGCCGTCTGAA
TTTGACCTGAGCGCATTTTTACGCGCCGGAGAAAACCGCCTCGCGGTGATGGT
GCTGCGTTGGAGTGACGGCAGTTATCTGGAAGATCAGGATATGTGGCGGATG
AGCGGCATTTTCCGTGACGTCTCGTTGCTGCATAAACCGACTACACAAATCAG
CGATTTCCATGTTGCCACTCGCTTTAATGATGATTTCAGCCGCGCTGTACTGGA
GGCTGAAGTTCAGATGTGCGGCGAGTTGCGTGACTACCTACGGGTAACAGTTT
CTTTATGGCAGGGTGAAACGCAGGTCGCCAGCGGCACCGCGCCTTTCGGCGGT
GAAATTATCGATGAGCGTGGTGGTTATGCCGATCGCGTCACACTACGTCTGAA
CGTCGAAAACCCGAAACTGTGGAGCGCCGAAATCCCGAATCTCTATCGTGCGG
TGGTTGAACTGCACACCGCCGACGGCACGCTGATTGAAGCAGAAGCCTGCGA
TGTCGGTTTCCGCGAGGTGCGGATTGAAAATGGTCTGCTGCTGCTGAACGGCA
AGCCGTTGCTGATTCGAGGCGTTAACCGTCACGAGCATCATCCTCTGCATGGT
CAGGTCATGGATGAGCAGACGATGGTGCAGGATATCCTGCTGATGAAGCAGA
ACAACTTTAACGCCGTGCGCTGTTCGCATTATCCGAACCATCCGCTGTGGTAC
ACGCTGTGCGACCGCTACGGCCTGTATGTGGTGGATGAAGCCAATATTGAAAC
CCACGGCATGGTGCCAATGAATCGTCTGACCGATGATCCGCGCTGGCTACCGG
CGATGAGCGAACGCGTAACGCGAATGGTGCAGCGCGATCGTAATCACCCGAG
TGTGATCATCTGGTCGCTGGGGAATGAATCAGGCCACGGCGCTAATCACGACG
CGCTGTATCGCTGGATCAAATCTGTCGATCCTTCCCGCCCGGTGCAGTATGAA
GGCGGCGGAGCCGACACCACGGCCACCGATATTATTTGCCCGATGTACGCGCG
CGTGGATGAAGACCAGCCCTTCCCGGCTGTGCCGAAATGGTCCATCAAAAAAT
GGCTTTCGCTACCTGGAGAGACGCGCCCGCTGATCCTTTGCGAATACGCCCAC
GCGATGGGTAACAGTCTTGGCGGTTTCGCTAAATACTGGCAGGCGTTTCGTCA
GTATCCCCGTTTACAGGGCGGCTTCGTCTGGGACTGGGTGGATCAGTCGCTGA
TTAAATATGATGAAAACGGCAACCCGTGGTCGGCTTACGGCGGTGATTTTGGC
GATACGCCGAACGATCGCCAGTTCTGTATGAACGGTCTGGTCTTTGCCGACCG
CACGCCGCATCCAGCGCTGACGGAAGCAAAACACCAGCAGCAGTTTTTCCAGT
TCCGTTTATCCGGGCAAACCATCGAAGTGACCAGCGAATACCTGTTCCGTCAT
AGCGATAACGAGCTCCTGCACTGGATGGTGGCGCTGGATGGTAAGCCGCTGG
CAAGCGGTGAAGTGCCTCTGGATGTCGCTCCACAAGGTAAACAGTTGATTGAA
CTGCCTGAACTACCGCAGCCGGAGAGCGCCGGGCAACTCTGGCTCACAGTAC
GCGTAGTGCAACCGAACGCGACCGCATGGTCAGAAGCCGGGCACATCAGCGC
CTGGCAGCAGTGGCGTCTGGCGGAAAACCTCAGTGTGACGCTCCCCGCCGCGT
CCCACGCCATCCCGCATCTGACCACCAGCGAAATGGATTTTTGCATCGAGCTG |

SEQUENCE LISTING

```
GGTAATAAGCGTTGGCAATTTAACCGCCAGTCAGGCTTTCTTTCACAGATGTG
GATTGGCGATAAAAAACAACTGCTGACGCCGCTGCGCGATCAGTTCACCCGTG
CACCGCTGGATAACGACATTGGCGTAAGTGAAGCGACCCGCATTGACCCTAAC
GCCTGGGTCGAACGCTGGAAGGCGGCGGGCCATTACCAGGCCGAAGCAGCGT
TGTTGCAGTGCACGGCAGATACACTTGCTGATGCGGTGCTGATTACGACCGCT
CACGCGTGGCAGCATCAGGGGAAAACCTTATTTATCAGCCGGAAAACCTACC
GGATTGATGGTAGTGGTCAAATGGCGATTACCGTTGATGTTGAAGTGGCGAGC
GATACACCGCATCCGGCGCGGATTGGCCTGAACTGCCAGCTGGCGCAGGTAG
CAGAGCGGGTAAACTGGCTCGGATTAGGGCCGCAAGAAAACTATCCCGACCG
CCTTACTGCCGCCTGTTTTGACCGCTGGGATCTGCCATTGTCAGACATGTATAC
CCCGTACGTCTTCCCGAGCGAAAACGGTCTGCGCTGCGGGACGCGCGAATTGA
ATTATGGCCCACACCAGTGGCGCGGCGACTTCCAGTTCAACATCAGCCGCTAC
AGTCAACAGCAACTGATGGAAACCAGCCATCGCCATCTGCTGCACGCGGAAG
AAGGCACATGGCTGAATATCGACGGTTTCCATATGGGGATTGGTGGCGACGAC
TCCTGGAGCCCGTCAGTATCGGCGAATTACAGCTGAGCGCCGGTCGCTACCA
TTACCAGTTGGTCTGGTGTCAAAAATAA

SEQ ID NO 2: β-galactosidase protein sequence E. Coli
MSFTLTNKNVIFVAGLGGIGLDTSKELLKRDPVVLQRRDWENPGVTQLNRLAAHP
PFASWRNSEEARTDRPSQQLRSLNGEWRFAWFPAPEAVPESWLECDLPEADTVV
VPSNWQMHGYDAPIYTNVTYPITVNPPFVPTENPTGCYSLTFNVDESWLQEGQTR
IIFDGVNSAFHLWCNGRWVGYGQDSRLPSEFDLSAFLRAGENRLAVMVLRWSDG
SYLEDQDMWRMSGIFRDVSLLHKPTTQISDFHVATRFNDDFSRAVLEAEVQMCG
ELRDYLRVTVSLWQGETQVASGTAPFGGEIIDERGGYADRVTLRLNVENPKLWS
AEIPNLYRAVVELHTADGTLIEAEACDVGFREVRIENGLLLLNGKPLLIRGVNRHE
HHPLHGQVMDEQTMVQDILLMKQNNFNAVRCSHYPNHPLWYTLCDRYGLYVV
DEANIETHGMVPMNRLTDDPRWLPAMSERVTRMVQRDRNHPSVIIWSLGNESGH
GANHDALYRWIKSVDPSRPVQYEGGGADTTATDIICPMYARVDEDQPFPAVPKW
SIKKWLSLPGETRPLILCEYAHAMGNSLGGFAKYWQAFRQYPRLQGGFVWDWV
DQSLIKYDENGNPWSAYGGDFGDTPNDRQFCMNGLVFADRTPHPALTEAKHQQ
QFFQFRLSGQTIEVTSEYLFRHSDNELLHWMVALDGKPLASGEVPLDVAPQGKQL
IELPELPQPESAGQLWLTVRVVQPNATAWSEAGHISAWQQWRLAENLSVTLPAAS
HAIPHLTTSEMDFCIELGNKRWQFNRQSGFLSQMWIGDKKQLLTPLRDQFTRAPL
DNDIGVSEATRIDPNAWVERWKAAGHYQAEAALLQCTADTLADAVLITTAHAW
QHQGKTLFISRKTYRIDGSGQMAITVDVEVASDTPHPARIGLNCQLAQVAERVNW
LGLGPQENYPDRLTAACFDRWDLPLSDMYTPYVFPSENGLRCGTRELNYGPHQW
RGDFQFNISRYSQQQLMETSHRHLLHAEEGTWLNIDGFHMGIGGDDSWSPSVSAE
LQLSAGRYHYQLVWCQK SEQ ID NO 3: RIG-I helicase Homo Sapiens
MTTEQRRSLQAFQDYIRKTLDPTYILSYMAPWFREEEVQYIQAEKNNKGPMEAAT
LFLKFLLELQEEGWFRGFLDALDHAGYSGLYEAIESWDFKKIEKLEEYRLLLKRL
QPEFKTRIIPTDIISDLSECLINQECEEILQICSTKGMMAGAEKLVECLLRSDKENWP
KTLKLALEKERNKFSELWIVEKGIKDVETEDLEDKMETSDIQIFYQEDPECQNLSE
NSCPPSEVSDTNLYSPFKPRNYQLELALPAMKGKNTIICAPTGCGKTFVSLLICEHH
LKKFPQGQKGKVVFFANQIPVYEQQKSVFSKYFERHGYRVTGISGATAENVPVEQ
IVENNDIIILTPQILVNNLKKGTIPSLSIFTLMIFDECHNTSKQHPYNMIMFNYLDQK
LGGSSGPLPQVIGLTASVGVGDAKNTDEALDYICKLCASLDASVIATVKHNLEELE
QVVYKPQKFFRKVESRISDKFKYIIAQLMRDTESLAKRICKDLENLSQIQNREFGT
QKYEQWIVTVQKACMVFQMPDKDEESRICKALFLYTSHLRKYNDALIISEHARM
KDALDYLKDFFSNVRAAGFEEIEQDLTQRFEEKLQELESVSRDPSNENPKLEDLCF
ILQEEYHLNPETITILFVKTRALVDALKNWIEGNPKLSFLKPGILTGRGKTNQNTG
MTLPAQKCILDAFKASGDHNILIATSVADEGIDIAQCNLVILYEYVGNVIKMIQTR
GRGRARGSKCFLLTSNAGVIEKEQINMYKEKMMNDSILRLQTWDEAVFREKILHI
QTHEKFIRDSQEKPKPVPDKENKKLLCRKCKALACYTADVRVIEECHYTVLGDAF
KECFVSRPHPKPKQFSSFEKRAKIFCARQNCSHDWGIHVKYKTFEIPVIKIESFVVE
DIATGVQTLYSKWKDFHFEKIPFDPAEMSK SEQ ID NO 4: EPO mus musculus
ATGGGGGTGCCCGAACGTCCCACCCTGCTGCTTTTACTCTCCTTGCTACTGATT
CCTCTGGGCCTCCCAGTCCTCTGTGCTCCCCACGCCTCATCTGCGACAGTCGA
GTTCTGGAGAGGTACATCTTAGAGGCCAAGGAGGCAGAAAATGTCACGATGG
GTTGTGCAGAAGGTCCCAGACTGAGTGAAAATATTACAGTCCCAGATACCAA
AGTCAACTTCTATGCTTGGAAAAGAATGGAGGTGGAAGAACAGGCCATAGAA
GTTTGGCAAGGCCTGTCCCTGCTCTCAGAAGCCATCCTGCAGGCCCAGGCCCT
GCTAGCCAATTCCTCCCAGCCACCAGAGACCCTTCAGCTTCATATAGACAAAG
CCATCAGTGGTCTACGTAGCCTCACTTCACTGCTTGGGTACTGGGAGCTCAG
AAGGAATTGATGTCGCCTCCAGATACCACCCCACCTGCTCCACTCCGAACACT
CACAGTGGATACTTCTGCAAGCTCTTCCGGGTCTACGCCAACTTCCTCCGGG
GGAAACTGAAGCTGTACACGGGAGAGGTCTGCAGGAGAGGGGACAGGTGA SEQ ID NO 5: Firefly luciferase
ATGCACATATCGAGGTGAACATCACGTACGCGGAATACTTCGAAATGTCCGTT
CGGTTGGCAGAAGCTATGAAACGATATGGGCTGAATACAAATCACAGAATCG
TCGTATGCAGTGAAAACTCTCTTCAATTCTTTATGCCGGTGTTGGGCGCGTTAT
TTATCGGAGTTGCAGTTGCGCCCGCGAACGACATTTATAATGAACGTAAGCAC
CCTCGCCATCAGACCAAAGGGAATGACGTATTTAATTTTTAAGGTGAATTGCT
```

```
CAACAGTATGAACATTTCGCAGCCTACCGTAGTGTTTGTTTCCAAAAAGGGGT
TGCAAAAAATTTTGAACGTGCAAAAAAAATTACCAATAATCCAGAAAATTATT
ATCATGGATTCTAAAACGGATTACCAGGGATTTCAGTCGATGTACACGTTCGT
CACATCTCATCTACCTCCCGGTTTTAATGAATACGATTTTGTACCAGAGTCCTT
TGATCGTGACAAAACAATTGCACTGATAATGAATTCCTCTGGATCTACTGGGT
TACCTAAGGGTGTGGCCCTTCCGCATAGAACTGCCTGCGTCAGATTCTCGCAT
GCCAGGTATGTCGTATAACAAGAGATTAAGTAATGTTGCTACACACATTGTAG
AGATCCTATTTTTGGCAATCAAATCATTCCGGATACTGCGATTTTAAGTGTTGT
TCCATTCCATCACGGTTTTGGAATGTTTACTACACTCGGATATTTGATATGTGG
ATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTT
CGCCAAAAGCACTCTGATTGACAAATACGATTTATCTAATTTACACGAAATTG
CTTCTGGGGCGCACCTCTTTCGAAAGAAGTCGGGGAAGCGGTTGCAAAACG
GTGAGTTAAGCGCATTGCTAGTATTTCAAGGCTCTAAAACGGCGCGTAGCTTC
CATCTTCCAGGGATACGACAAGGTATGGGCTCACTGAGACTACATCAGCTAT
TCTGATTACACCCGAGGGGGATGATAAACCGGGCGCGGTCGGTAAAGTTGTTC
CATTTTTTGAAGCGAAGGTTGTGGATCTGGATACCGGGAAAACGCTGGGCGTT
AATCAGAGAGGCGAATTATGTGTCAGAGGACCTATGATTATGTCCGGTTATGT
AAACAATCCGGAAGCGACCAACGCCTTGATTGACAAGGATGGATGGCTACAT
TCTGGAGACATAGCTTACTGGGACGAAGACGAACACTTCTTCATAGTTGACCG
CTTGAAGTCTTTAATTAAATACAAAGGATATCAGGTAATGAAGATTTTTACAT
GCACACACGCTACAATACCTGTAGGTGGCCCCCGCTGAATTGGAATCGATATT
GTTACAACACCCCAACATCTTCGACGCGGGCGTGGCAGGTCTTCCCGACGATG
ACGCCGGTGAACTTCCCGCCGCCGTTGTTGTTTGGAGCACGGAAAGACGATG
ACGGAAAAAGAGATCGTGGATTACGTCGCCAGTAAATGAATTCGTTTTACGTT
ACTCGTACTACAATTCTTTTCATAGGTCAAGTAACAACCGCGAAAAAGTTGCG
CGGAGGAGTTGTGTTTGTGGACGAAGTACCGAAAGGTCTTACCGGAAAACTC
GACGCAAGAAAAATCAGAGAGATCCTCATAAAGGCCAAGAAGGGCGGAAAG
TCCAAATTGTAAAATGTAACTGTATTCAGCGATGACGAAATTCTTAGCTATTG
TAATATTATATGCAAATTGATGAATGGTAATTTTGTAATTGTGGGTCACTGTAC
TATTTTAACGAATAATAAAATCAGGTATAGGTAACTAAAAA
```

The invention claimed is:

1. A method for gene delivery, comprising more than one administration to a subject of a composition comprising a tetrafunctional non-ionic amphiphilic block copolymer as a vehicle for intracellular delivery of capped unmodified mRNA or uncapped unmodified mRNA; wherein said tetrafunctional non-ionic amphiphilic block copolymer is selected from the group consisting of:

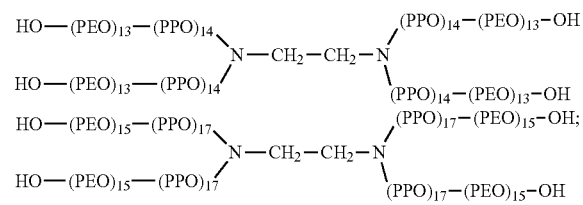

and mixtures thereof.

2. The method according to claim 1, wherein said mRNA is an uncapped unmodified mRNA.

3. The method according to claim 1, wherein said mRNA is a capped unmodified mRNA.

4. The method according to claim 1, wherein said capped unmodified mRNA or uncapped unmodified mRNA is a messenger $_{5'ppp}$RNA; $_{5'pp}$RNA; $_{5'p}$RNA, or $_{5'OH}$RNA.

5. The method according to claim 1, wherein said tetrafunctional non-ionic amphiphilic block copolymer is

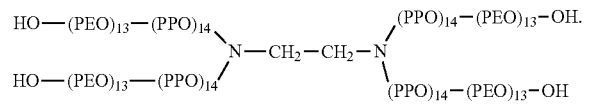

6. The method according to claim 1, wherein said tetrafunctional non-ionic amphiphilic block copolymer is

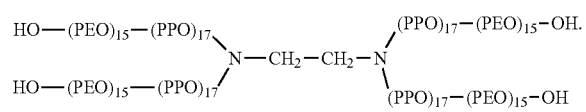

7. The method according to claim 1, wherein the composition comprising a tetrafunctional non-ionic amphiphilic block copolymer is administered by intramuscular injection.

8. The method according to claim 1, wherein the composition comprising a tetrafunctional non-ionic amphiphilic block copolymer is administered by intramuscular injection and the mRNA is a capped unmodified mRNA.

9. The method according to claim 1, wherein the composition comprising a tetrafunctional non-ionic amphiphilic block copolymer is administered by intramuscular injection and the mRNA is an uncapped unmodified mRNA.

10. A composition comprising a tetrafunctional non-ionic amphiphilic block copolymer in combination with at least one uncapped unmodified mRNA; wherein said tetrafunctional non-ionic amphiphilic block copolymer is selected from the group consisting of:

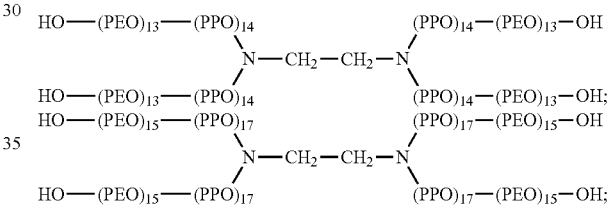

and mixtures thereof.

11. A kit for intracellular delivery of uncapped unmodified mRNA, comprising:
(i) at least one tetrafunctional non-ionic amphiphilic block copolymer; and
(ii) at least one uncapped unmodified mRNA;
wherein said tetrafunctional non-ionic amphiphilic block copolymer is selected from the group consisting of:

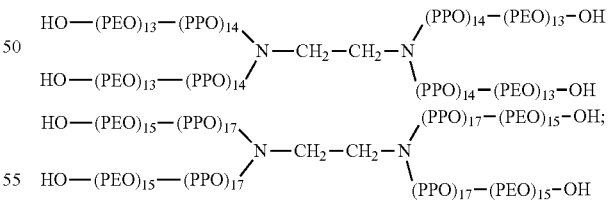

and mixtures thereof.

* * * * *